United States Patent
Stern et al.

(10) Patent No.: US 6,555,651 B2
(45) Date of Patent: *Apr. 29, 2003

(54) LIGAND BINDING SITE OF RAGE AND USES THEREOF

(75) Inventors: David Stern, Great Neck, NY (US); Shi Du Yan, New York, NY (US); Ann Marie Schmidt, Franklin Lakes, NJ (US); Ira Lamster, Wyckoff, NJ (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/948,131

(22) Filed: Oct. 9, 1997

(65) Prior Publication Data

US 2001/0053357 A1 Dec. 20, 2001

(51) Int. Cl.⁷ .................. A61K 38/00; C07K 16/00; C07K 17/00; C07K 5/00
(52) U.S. Cl. ........................ 530/324; 530/300
(58) Field of Search ............... 530/300, 387.1, 530/324, 350

(56) References Cited

U.S. PATENT DOCUMENTS

| | | |
|---|---|---|
| 5,585,344 A | 12/1996 | Vlassara et al. |
| 5,688,653 A | 11/1997 | Ulrich et al. |
| 5,864,018 A * | 1/1999 | Morser .................... 530/387.1 |

FOREIGN PATENT DOCUMENTS

| | | |
|---|---|---|
| WO | 9520979 | 8/1995 |
| WO | 9726913 | 7/1997 |
| WO | 9739121 | 10/1997 |
| WO | WO9739125 | 10/1997 |

OTHER PUBLICATIONS

Liu et al., Biochem. & Biophys. Res. Comm. 237:37–40, 1997.*
Genbank Accession No. A42879, 1992.*
Renard, Mol. Pharm., 52:54–62, 1997.*
Weber et al, Brain Res. 791:11–17, 1998.*
Liu et al, Biochem. Biophys.Res.Commun. 237:37–40, 1997.*
Miyata et al, Kidney Intl. 51:1170–1181, 1997.*
Goodman et al, The Pharm. Basis of Ther., 8th ed., p.11, 1990.*
Breslow, J.L (1996) Mouse Models of Atherosclerosis, Science 272: 685 (Exhibit 5).

Brett, J. et al., (1993) "Survey of the Distribution of a Newly Characteriszed Receptor for the advanced Glycosylation Endproducts in Tissues" Am. J. Pathol., 143:1699–1712, (Exhibit 6).
Gibbons, G.H. et al. (1996) "Molecular Therapies for Vascular Disease," Science, 272:689–693 (Exhibit 7).
Lander, H.M. et al. "Activation of the Receptor for Advanced Glycation Endproducts triggers a p21ras– dependent MAP Kinase Pathway Regulated by Oxidant Stress," J.Biol.Chem., 272:17810–17814 (Exhibit 8).
Loo, D., et al. (1993) Apoptosis is Induced by β–amyloid in cultured central nervous system neurons, P.N.A.S. (USA), 90:7951–7955 (Exhibit 9).
Mattson, et al., Amyloid ox–tox transducers. Nature, 238:674–675 (Exhibit 10); Aug. 1996.
Miyata, T., O. Hori, J.H. Zhang, S.D. Yan, L. Ferran, Y. Iida, and A.M. Schmidt, The Receptor for Advanced Glycation Endproducts (RAGE) mediates the interaction of AGE–$β_2$–Microglobulin with human mononuclear phagocytes via an oxidant–sensitive pathway: impllications for the pathogenesis of dialysis–related amyloidoses. J. Clin. Invest. 98: 1088–1094, 1996 (Exhibit 11).
Neeper, M., Schmidt, A.M., Brett, J., Yan, S.D., Wang, F., Pan, Y.C., Elliston, K., Stern, D., and Shaw, A. Cloning and expression of RAGE: a cell surface receptor for advanced glycosylation end products of proteins. J. Biol. Chem. 267:14998–15004, 1992 (Exhibit 12).
Park, L., Raman, K.G., Lee, K.J., Lu, Y., Ginsberg, M.D., Ferran, L., Stern, D. and Schmidt, A.M. A murine model of accelerated diabetic atherosclerosis: suppression by soluble receptor for advanced glycation endproducts. Circulation Supplement, 1997 (Exhibit 13).

(List continued on next page.)

*Primary Examiner*—Gary Kunz
*Assistant Examiner*—Sharon Turner
(74) *Attorney, Agent, or Firm*—John P. White; Cooper & Dunham LLP

(57) ABSTRACT

The present method provides for an isolated peptide having an amino acid sequence corresponding to the amino acid sequence of a V-domain of a receptor for advanced glycation endproduct (RAGE). The present invention also provides for an isolated peptide having an amino acid sequence A-Q-N-I-T-A-R-I-G-E-P-L-V-L-K-C-K-G-A-P-K-K-P-P-Q-R-L-E-W-K (SEQ. ID No: 1). The present invention provides for a pharmaceutical composition comprising a therapeutically effect amount of an isolated peptide having an amino acid sequence corresponding to the amino acid sequence of a V-domain of RAGE. The present invention also provides for a method for inhibiting interaction of an amyloid-β peptide with a receptor for advanced glycation end product which is on the surface of a cell, which comprises contacting the cell with the peptide or a functionally equivalent agent, wherein the peptide or agent is capable of inhibiting interaction of the amyloid-β peptide with the receptor for advanced glycation end product, and the peptide or agent is present in an amount effective to inhibit interaction of the amyloid-β peptide with the receptor for advanced glycation endproduct.

4 Claims, 1 Drawing Sheet

OTHER PUBLICATIONS

Schmidt, A.M., O. Hori, J. Chen, J.F. Li, J. Crandall, J. Zhang, R. Cao, S.D. Yan, J. Brett and D. Stern. Advanced glycation endproducts interacting with their endothelial receptor induce expression of vascular cell adhesion molecule–1 (VCAM–1): a potential mechanism for the accelerated vasculopathy of diabetes. J. Clin. Invest. 96:1395–1403, 1995 (Exhibit 14).

Schmidt, A.M., Yan, S.D., Brett, J. Mora, R. and Stern, D. Regulation of mononuclear phagocyte migration by cell surface binding proteins for advanced glycosylation endproducts. J. Clin. Invest. 92:2155–2168, 1993 (Exhibit 15).

Schmidt, A.M., Hasu, M., Popov, D., Zhang, J.H., Yan, S.D., Brett, J., Cao, R., Kuwabara, K., Costache, G., Simionescu, N., Simonescu, M., and Stern, D. The receptor for Advanced Glycation Endproducts (AGEs) has a central role in vessel wall interactions and gene activation in response to AGEs in the intravascular space. PNAS (USA) 91:8807–8811, 1994 (Exhibit 16).

Schmidt, A.M., Vianna, M., Gerlach, M., Brett, J., Ryan, J., Kao, J., Esposito, C., Hegary, H. Hurley, W., Clauss, M., Wang, F., Pan, Y.C., Tsang, T.C., and Stern, D. Isolation and characterization of binding proteins for advanced glycosylation endproducts from lung tissue which are present on the endothelial cell surface. J. Biol. Chem. 267:14987–14997, 1992 (Exhibit 17).

Wautier, J.L., C. Zoukourian, O. Chappey, M.P. Wautier, P.J. Guillausseau, R. Cao, O. Hori, D. Stern and A.M. Schmidt. Receptor–mediated endothelial cell dysfunction in diabetic vasculopathy: soluble receptor for advanced glycation endproducts blocks hyperpermeability. J. Clin. Invest. 97:238–243, 1996 (Exhibit 18).

Wu, J., Rogers, L., Stern, D., Schmidt, A.M. and Chiu, D.T.W., The soluble receptor for Advanced Glycation Endproducts (sRAGE) ameliorates impared wound healing in diabetic mice.Abstract booklet, Plastic Surgery Research Council. Abstract #77, p.43, 1997(Exhibit 19).

Yan, S.D., Schmidt, A.M. Anderson, G., Zhang, J., Brett, J., Zou, Y.S., Pinsky, D., and Stern, D. Enhanced cellular oxidant stress by the interaction of advanced glycation endproducts with their receptors/binding proteins. J. Biol. Chem. 269:9889–9897, 1994 (Exhibit 20).

Yan, S. D., X. Chen, J. Fu, M. Chen, H. Zhu, A. Roher, T. Slattery, M. Nagashima, J. Morser, A. Migheli, P. Nawroth, G. Godman, D.Stern and A.M. Schmidt. RAGE and amyloid–β peptide neurotoxicity in Alzheimer's disease. Nature 382:685–691, 1996 (Exhibit 21).

Yan, S. D., Zhu, H., Fu, J., Yan, S.F., Roher, A., Tourtellotte, W., Rajavashisth, T., Chen, X., Stern, D. and Schmidt, A.M. Amyloid–beta peptide–RAGE interaction elicits nauronal expression of M–CSF: a proinflammatory pathway in Alzheimer's disease. Proc. Natl. Acad. Sci. 94:5296–5301, 1997 (Exhibit 22).

Brownlee, M. (1992). Glycation products and the pathogenesis of diabetic complications. *Diabetes Care* 15(12):1835–1842.

Fu, M–X., et al., (1996) "The Advanced Glycation Endproduct, $N^e$–(Carboxymethyl)lysine is a product of both lipid peroxidation and glycoxidation reactions" *J. Biol. Chem.*, 271:9982–9986.

Hofmann M, Drury S, Caifeng F, Qu W, Lu Y, Avila C, Kambhan N, Slattery T, McClary J, Nagashima M, Morser J, Stern D, Schmidt A–M: RAGE mediates a novel proinflammatory axis: the cell surface receptor for S100/calgranulin polypeptides. *Cell* 1999;97:889–901.

Hori, et al., "The Receptor for Advanced Glycation Endproducts: Implications for the Development of Diabetic Vascular Disease. Fundam. Clin. Cardiol." In: The Endothelium in Clinical Practice. Jan. 1997, Chapter 11, pp. 311–329.

Hori O, Brett J, Nagashima M, Nitecki D, Morser J, Stern DM, Schmidt AM: RAGE is a cellular binding site for amphoterin: mediation of neurite outgrowth and co–expression of RAGE and amphoterin in the developing nervous system. *J Biol Chem* 1995;270:25752–25761.

Lander, H. L., et al. (1997) "Activation of the Receptor for Advanced Glycation Endproducts triggers a MAP Kinase pathway regulated by oxidant stress" *J. Biol. Chem.*, 272:17810–17814.

Li, J. and Schmidt, A. M. (1997) "Characterization and functional analysis of the promoter of RAGE, the Receptor for Advanced Glycation Endproducts" *J. Biol. Chem.*, 272:16498–16506.

Park, L., et al. (1997). A murine model of accelerated diabetic atherosclerosis: suppression by soluble receptor for advanced glycation endproducts. *Circulation Supplement*. Abstract 3079.

Renard, C., et al. (1997). Recombinant advanced glycation end product receptor pharmacokinetics in normal and diabetic rats. Mol. Pharm. 52: 54–62.

Ritthaler, et al. (1995) Expression of receptors for advanced glycation end products in peripheral occulsive vascular disease. Am. J. Path. 146:688–694.

Schmidt, A. M., et al. (Nov. 9–12, 1997) "The V–Domain of Receptor for Advanced Glycation Endproducts (RAGE) mediates binding of AGEs: a novel target for therapy of diabetes" *Circulation Supplement,* 96:#194. Abstract.

Schmidt, A. M., et al. (1994) "The endothelial cell binding site for advanced glycation endproducts consists of a complex: an integral membrane protein and a lactoferrin–like polypeptide" *J. Biol. Chem.,* 269:9882–9888.

Schmidt, A–M, et al. (1994) "Cellular receptors for advanced glycation end products" *Arterioscler. Thromb.,* 14:1521–1528.

Schmidt A–M, Yan S–D, Wautier J–L, Stern DM: Activation of RAGE: A mechanism for chronic vascular dysfunction in diabetic vasculopathy atherosclerosis. *Circ Res* 1999;84:489–497.

Stern et al.,PCT International Publication No. WO 97/26913, published Jul. 31, 1997, PCT International Application No. PCT/US97/00857.

Vlassara, H., et al., (1995) "Identification of Galectin–2 as a high affinity binding protein for Advanced Glycation Endproducts (AGE): a new member of the AGE–Receptor complex" *Molecular Medicine*, 1:634–646.

Wautier, J.–L., et al. (1996). Interaction of diabetic erythrocytes bearing advanced glycation endproducts with the endothelial receptor AGE induces generation of reactive oxygen intermediates and cellular dysfunction. *Circulation Supplement* 94(8): #4139.

Yan S–D, Chen X, Chen M, Zhu H, Roher A, Slattery T, Zhao L, Nagashima M, Morser J, Migheli A, Nawroth P, Stern DM, Schmidt A–M: RAGE and amyloid–beta peptide neurotoxicity in Alzheimer's disease. *Nature* 1996;382:685–691.

* cited by examiner

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 30 amino acids
      (B) TYPE: amino acid (C) STRANDEDNESS: single
        (D) TOPOLOGY: linear (ii) MOLECULE TYPE: peptide (xi) SEQUENCE DESCRIPTION: SEQ ID NO:1:

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys
            20                  25                  30

(2) INFORMATION FOR SEQ ID NO:2:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Gly Gln Asn Ile Thr Ala Arg Ile Gly Glu Pro Leu Val Leu Ser Cys
1               5                   10                  15

Lys Gly Ala Pro Lys Lys Pro Pro Gln Gln Leu Glu Trp Lys
            20                  25                  30

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Gly Gln Asn Ile Thr Ala Arg Ile Gly Glu Pro Leu Met Leu Ser Cys
1               5                   10                  15

Lys Ala Ala Pro Lys Lys Pro Thr Gln Lys Leu Glu Trp Lys
            20                  25                  30

(2) INFORMATION FOR SEQ ID NO:4:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Asp Gln Asn Ile Thr Ala Arg Ile Gly Lys Pro Leu Val Leu Asn Cys
1               5                   10                  15

Lys Gly Ala Pro Lys Lys Pro Pro Gln Gln Leu Glu Trp Lys
            20                  25                  30

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear -continued

```
    (ii) MOLECULE TYPE: peptide (xi) SEQUENCE DESCRIPTION: SEQ ID NO:5:

Ala Gln Asn Ile Thr Ala Arg Ile Gly Glu
1               5                   10
```

LIGAND BINDING SITE OF RAGE AND USES THEREOF

The invention disclosed herein was made with Government support under USPHS Grants No. AG00690, AG00603, HL56881 from the Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of the specification immediately following the Experimental Procedures section and preceding the claims sections. The disclosures of these publications in their entireties are hereby incorporated by reference into this application in order to more fully describe the state of the art as known to those skilled therein as of the date of the invention described and claimed herein.

Ischemic heart disease is a leading cause of morbidity and mortality in the general population, but especially in patients with diabetes. The prevalence of coronary artery disease is as high as 55% in adult patients with diabetes (Robertson and Strong, 1968). Indeed, data from the Framingham Heart Study demonstrate that mortality from cardiovascular disease in non-insulin dependent diabetes (NIDDM) is more than doubled in diabetic men and more than quadrupled in diabetic women when compared with nondiabetic control subjects (Kannel and McGee, 1979). In addition to increased prevalence, studies have shown that atherosclerosis in diabetic patients is clearly more accelerated and extensive. In one autopsy series, for example, patients with diabetes were found to have more severe disease of the left anterior descending coronary artery (Waller et al., 1980), a higher incidence of two and three-vessel disease (Crall and Roberts, 1978), and a greater diffuseness of distribution of atherosclerotic lesions (Hamby et al., 1976). These findings were confirmed by coronary angiography in symptomatic patients (Pyorala et al., 1978).

The reasons for accelerated atherosclerosis in the setting of diabetes are numerous. However, even after correction for dyslipidemia, hypertension and obesity, multivariate analysis studies have indicated that diabetic patients have an excess risk of cardiovascular disease relative to nondiabetic subjects (Kannel and McGee, 1979). For example, in the Nurses' Health Study of 1,500 diabetic subjects among a total of 115,000 women, the incidence of cardiovascular disease was 5-fold higher in the diabetic subjects regardless of their levels of cholesterol (Manson et al., 1991). These data suggest that factors unique to the diabetic population play an important role.

The pathologic hallmarks of Alzheimer's disease (AD) are intracellular and extracellular accumulations of proteins, progression of which is closely correlated with eventual neuronal dysfunction and clinical dementia (for reviews see Goedert, 1993; Haass et al., 1994; Kosik, 1994; Trojanowski et al., 1994; Wischik, 1989). Amyloid-β peptide (Aβ), which is the principal component of extracellular deposits in AD, both in senile/diffuse plaques and in cerebral vasculature, actively influences cellular functions as indicated by several lines of evidence: Aβ has been shown to promote neurite outgrowth, generate reactive oxygen intermediates (ROIs), induce cellular oxidant stress, lead to neuronal cytotoxicity, and promote microglial activation (Behl et al., 1994; Davis et al., 1992; Hensley, et al., 1994; Koh, et al., 1990; Koo et al., 1993; Loo et al., 1993; Meda et al., 1995; Pike et al., 1993; Yankner et al., 1990). For Aβ to induce these multiple cellular effects, cell surfaces may contain a binding protein (s) which engages Aβ. In this context, several cell-associated proteins, as well as sulfated proteoglycans, can interact with Aβ. These include: substance P receptor, the serpin-enzyme complex (SEC) receptor, apolipoprotein E, apolipoprotein J (clusterin), transthyretin, alpha-1 anti-chymotrypsin, β-amyloid precursor protein, and sulphonates/heparin sulfates (Abraham et al., 1988; Fraser et al., 1992; Fraser et al., 1993; Ghiso et al., 1993; Joslin et al., 1991; Kimura et al., 1993; Kisilevsky et al., 1995; Strittmatter et al., 1993a; Strittmatter et al., 1993b; Schwarzman et al., 1994; Snow et al., 1994; Yankner et al., 1990). Of these, the substance P receptor and SEC receptor might function as neuronal cell surface receptors for Aβ, though direct evidence for this is lacking (Fraser et al., 1993; Joslin et al., 1991; Kimura et al., 1993; Yankner et al., 1990). In fact, the role of substance P receptors is controversial, and it is not known whether Aβ alone interacts with the receptor, or if costimulators are also required (Calligaro et al., 1993; Kimura et al., 1993; Mitsuhashi et al., 1991) and the SEC receptor has yet to be fully characterized. Amyloid-β peptide (Aβ) is central to the pathology of Alzheimer's disease (AD), primarily because of its neurotoxic effects which involve induction of cellular oxidant stress.

SUMMARY OF THE INVENTION

The present method provides for an isolated peptide having an amino acid sequence corresponding to the amino acid sequence of a V-domain of a receptor for advanced glycation endproduct (RAGE). The present invention also provides for an isolated peptide having an amino acid sequence A-Q-N-I-T-A-R-I-G-E-P-L-V-L-K-C-K-G-A-P-K-K-P-P-Q-R-L-E-W-K (SEQ ID No: 1). The present invention provides for a pharmaceutical composition comprising a therapeutically effect amount of an isolated peptide having an amino acid sequence corresponding to the amino acid sequence of a V-domain of RAGE and a pharmaceutically acceptable carrier. The present invention also provides for a method for inhibiting interaction of an amyloid-β peptide with a receptor for advanced glycation end product which is on the surface of a cell, which comprises contacting the cell with the peptide or a functionally equivalent agent, wherein the peptide or agent is capable of inhibiting interaction of the amyloid-β peptide with the receptor for advanced glycation end product, and the peptide or agent is present in an amount effective to inhibit interaction of the amyloid-β peptide with the receptor for advanced glycation endproduct.

The present invention also provides for a method for treating a subject with a condition associated with interaction of an amyloid-β peptide with a receptor for advanced glycation end product on a cell, which comprises administering to the subject the peptide or a functionally equivalent agent capable of inhibiting the interaction of the amyloid-β peptide with the receptor for advanced glycation end product, the peptide or the agent being present in an amount effective to inhibit the amyloid-β peptide interaction with the receptor, thereby treating the subject.

DETAILED DESCRIPTION OF THE INVENTION

Figure 1:
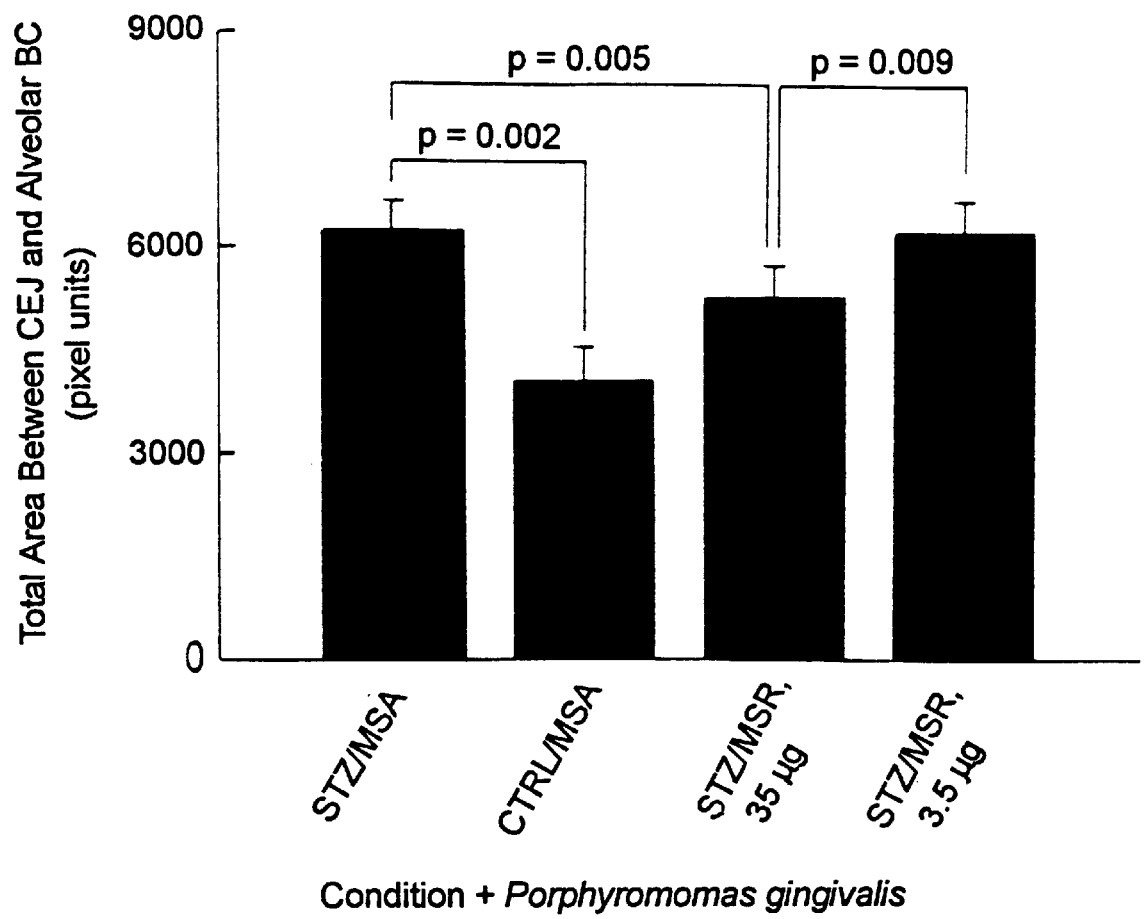
FIG 1. Measurements of alveolar bone loss in mice treated with sRAGE. See Example 2 in the Experimental Procedures. Statistical analysis=Group I vs. Group II-p=0.002; Group I vs. Group III-p=0.005; Group III vs. Group IV: p=0.009.

The present invention provides for an isolated peptide having an amino acid sequence corresponding to the amino acid sequence of a V-domain of a receptor for advanced glycation endproduct. The present invention also provides for a method of treating or ameliorating symptoms in a subject which are associated with a disease, wherein the disease is atherosclerosis, hypertension, impaired wound healing, periodontal disease, male impotence, retinopathy and diabetes and complications of diabetes, which comprises administering to the subject an amount of the isolated peptide of the present invention or an agent capable of inhibiting the interaction between amyloid-$\beta$ peptide and RAGE, effective to inhibit the interaction so as to treat or ameliorate the disease or condition in the subject. The method may also prevent such conditions from occurring in the subject.

In several embodiments of the present invention, a peptide having an amino acid sequence corresponding to the amino acid sequence of a V-domain of a RAGE or soluble RAGE is exemplified by the following amino acid sequences:

A-Q-N-I-T-A-R-I-G-E-P-L-V-L-K-C-K-G-A-P-K-K-P-P-Q-R-L-E-W-K (SEQ ID No: 1);

G-Q-N-I-T-A-R-I-G-E-P-L-V-L-S-C-K-G-A-P-K-K-P-P-Q-Q-L-E-W-K (SEQ ID No: 2);

G-Q-N-I-T-A-R-I-G-E-P-L-M-L-S-C-K-A-A-P-K-K-P-T-Q-K-L-E-W-K (SEQ ID No: 3);

D-Q-N-I-T-A-R-I-G-K-P-L-V-L-N-C-K-G-A-P-K-K-P-P-Q-Q-L-E-W-K (SEQ ID No: 4).

The present invention provides for an isolated peptide having an amino acid sequence which corresponds to the amino acid sequence of the first 1-112 amino acids of human RAGE (which is the V-domain of human RAGE), or which corresponds to amino acids 5-35 of the V-domain of human RAGE, or any other smaller portion of the V-domain of human RAGE.

Representative peptides of the present invention include but are not limited to peptides having an amino acid sequence which corresponds to amino acid numbers (2-30), (5-35), (10-40), (15-45), (20-50), (25-55), (30-60), (30-65), (10-60), (8-100), 14-75), (24-80), (33-75), (45-110) of human sRAGE protein.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Gutamic acid; G=Gly=Glycine; H=His=Histidine; I=Ile=Isoleucine; L=Leu=Leucine; K=Lys Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The present invention also encompasses a pharmaceutical composition which comprises a therapeutically effective amount of the peptide having an amino acid sequence corresponding to the amino acid sequence of a V-domain of a receptor for advanced glycation endproduct (RAGE) and a pharmaceutically acceptable carrier. The carrier may be a diluent, an aerosol, a topical carrier, an aqueous solution, a nonaqueous solution or a solid carrier. The carrier may be a polymer or a toothpaste. The pharmaceutical composition may comprise the peptide having an amino acid sequence corresponding to the amino acid sequence of a V-domain of a RAGE linked to a second peptide, wherein the second peptide may be an albumin, a globulin or a peptide chosen from a group of peptides, wherein each peptide of the group comprises a different length peptide, and wherein the sequence of each peptide corresponds to any sequence of amino acids taken from within amino acid number 31 through amino acid number 281 of the human sRAGE protien.

The present invention also encompasses a pharmaceutical composition which comprises a therapeutically effective amount of the peptide having an amino acid sequence corresponding to the amino acid sequence of a V-domain of a receptor for advanced glycation endproduct linked to an antibody or portion thereof. In one embodiment, the antibody may be capable of specifically binding to the receptor for advanced glycation endproduct. The antibody may be a monoclonal antibody, a polyclonal antibody. The portion or fragment of the antibody may comprise a $F_{ab}$ fragment or a $F_c$ fragment. The portion or fragment of the antibody may comprise a complementarity determining region or a variable region.

The present invention also provides for a method for inhibiting an amyloid-$\beta$ peptide's interaction with a receptor for advanced glycation end product when the receptor is on the surface of a cell, which comprises contacting the cell with an amount of an inhibitor of said interaction effective to inhibit interaction of the amyloid-$\beta$ peptide with the receptor for advanced glycation endproduct.

The cell may be a eukaryotic cell. The cell may be a cell of a subject. The subject may be a human. The cell may be a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell a ganglion cell or a stem cell. The cell may also be other kinds of cells not explicitly listed herein. The cell may be any human cell. The cell may be a normal cell, an activated cell, a neoplastic cell, a diseased cell or an infected cell.

In one embodiment, the inhibitor comprises a peptide, a peptidomimetic compound, a nucleic acid molecule, a small molecule, an organic compound, an inorganic compound, or an antibody or a fragment thereof. The inhibitor may be the isolated peptide having an amino acid sequence corresponding to the amino acid sequence of a V-domain of a receptor for advanced glycation endproduct. The inhibitor may be any of the compounds or compositions described herein.

The inhibitor may be a soluble V-domain of a receptor for advanced glycation endproduct. The inhibitor may comprise an antibody or fragment thereof. The antibody may be capable of specifically binding to the receptor for advanced glycation endproduct. The antibody may be a monoclonal antibody or a polyclonal antibody or a fragment of an antibody. The antibody fragment may comprise a Fab or Fc fragment. The fragment of the antibody may comprise a complementarity determining region.

In one embodiment, the inhibitor is capable of specifically binding to the amyloid-$\beta$ peptide.

The present invention also provides for a method for inhibiting degeneration of a neuronal cell which comprises contacting the cell with an inhibitor of the interaction of an amyloid-$\beta$ peptide with a receptor for advanced glycation end product so as to inhibit the interaction and thereby inhibit degeneration of the neuronal cell.

In another embodiment, the present invention provides for a method for inhibiting formation of an amyloid-β peptide fibril on a cell which comprises contacting the cell with an inhibitor of the interaction of an amyloid-β peptide with a receptor for advanced glycation end product so as to inhibit the interaction and thereby inhibit formation of the amyloid-β peptide fibril on a cell.

In another embodiment, the present invention provides for a method for inhibiting extracellular assembly of an amyloid-β peptide into a fibril which comprises contacting the amyloid-β peptide with an inhibitor of the interaction of an amyloid-β peptide with another amyloid-β peptide so as to inhibit the interaction and thereby inhibit extracellular assembly of an amyloid-β peptide into a fibril.

In another embodiment, the present invention provides for a method for inhibiting aggregation of amyloid-β peptide on the surface of a cell which comprises contacting the amyloid-β peptide with an inhibitor of the interaction of the amyloid-β peptide with a receptor for advanced glycation end product so as to inhibit the interaction and thereby inhibit aggregation of amyloid-β peptide on the surface of a cell.

In another embodiment, the present invention provides for a method for inhibiting infiltration of a microglial cell into senile plaques which comprises contacting the microglial cell with an inhibitor of the interaction of an amyloid-β peptide with a receptor for advanced glycation end product on the surface of the microglial cell, so as to inhibit the interaction and thereby inhibit infiltration of a microglial cell into senile plaques.

In another embodiment, the present invention provides for a method for inhibiting activation of a microglial cell by an amyloid-β peptide which comprises contacting the microglial cell with an inhibitor of the interaction of the amyloid-β peptide with a receptor for advanced glycation end product on the surface of the microglial cell so as to inhibit the interaction and thereby inhibit activation of a microglial cell.

In another embodiment, the present invention provides for a method for treating a subject with a condition associated with an interaction of an amyloid-β peptide with a receptor for advanced glycation end product on a cell, which comprises administering to the subject an inhibitor capable of inhibiting the interaction of the amyloid-β peptide with the receptor for advanced glycation end product, the inhibitor being present in an amount effective to inhibit the amyloid-β peptide interaction with the receptor, thereby treating the subject.

In another embodiment, the condition is diabetes, Alzheimer's Disease, senility, renal failure, hyperlipidemic atherosclerosis, neuronal cytotoxicity, Down's syndrome, dementia associated with head trauma, amyotrophic lateral sclerosis, multiple sclerosis, amyloidosis, an autoimmune disease, inflammation, a tumor, cancer, male impotence, wound healing, periodontal disease, neuopathy, retinopathy, nephropathy or neuronal degeneration. The subject may be a mammal. The mammal may be a human.

The administration may comprise intralesional, intraperitoneal, intramuscular or intravenous injection; infusion; liposome-mediated delivery; topical, nasal, oral, anal, subcutaneous, vaginal, sublingual, uretheral, transdermal, intrathecal, ocular or otic delivery. The condition may be associated with degeneration of a neuronal cell in the subject. The condition may be associated with formation of an amyloid-β peptide fibril. The condition may be associated with aggregation of amyloid-β peptide, with infiltration of a microglial cell into a senile plaque, or with activation of a microglial cell by an amyloid-β peptide.

The inhibitor may consists essentially of a portion of the peptide having an amino acid sequence corresponding to the amino acid sequence of a V-domain of a receptor for advanced glycation endproduct.

The inhibitor may comprises the pharmaceutical composition which comprises a peptide having an amino acid sequence corresponding to the amino acid sequence of a V-domain of a receptor for advanced glycation endproduct and a carrier.

The present invention provides for a method for evaluating the ability of an agent to inhibit binding of an amyloid-β peptide with a V-domain of a receptor for advanced glycation end product on the surface of a cell which comprises: (a) contacting the cell with the agent and amyloid-β peptide; (b) determining the amount of amyloid-β peptide bound to the cell, and (c) comparing the amount of bound amyloid-β peptide determined in step (b) with the amount determined in the absence of the agent, thus evaluating the ability of the agent to inhibit the binding of amyloid-β peptide to the V-domain of the receptor for advanced glycation end product on the surface of the cell.

In one embodiment, the cell is contacted with the agent and the amyloid-β peptide simultaneously. In another embodiment, the cell is contacted with the amyloid-β peptide and the agent. The cell may be a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell a ganglion cell or a stem cell.

The agent may comprises a peptide, a peptidomimetic compound, a nucleic acid molecule, a small molecule, an organic compound, an inorganic compound, or an antibody or a fragment thereof. The agent may be a peptide having an amino acid sequence corresponding to the amino acid sequence of a V-domain of a receptor for advanced glycation endproduct.

In one embodiment, the agent is a peptide having the amino acid sequence A-Q-N-I-T-A-R-I-G-E-P-L-V-L-K-C-K-G-A-P-K-K-P-P-Q-R-L-E-W-K (SEQ ID No: 1).

In another embodiment, the agent is a peptide having the amino acid sequence A-Q-N-I-T-A-R-I-G-E (SEQ ID No:. 5). In another embodiment, the agent is a soluble V-domain of a receptor for advanced glycation endproduct. The agent may also be a soluble extracellular portion of a receptor for advanced glycation end product. The agent may be an antibody or fragment thereof or is linked to an antibody or fragment thereof. The antibody may be capable of specifically binding to a receptor for advanced glycation endproduct. The antibody may be a monoclonal antibody. The antibody may be a polyclonal antibody. The fragment of the antibody may comprises a Fab or Fc fragment. The fragment of the antibody may comprise a complementarity determining region.

In one embodiment, the agent is capable of specifically binding to the amyloid-β peptide. In another embodiment, the agent is bound to a solid support. In another embodiment, the agent is expressed on the surface of a cell.

The present invention provides for a method for inhibiting activation of an NF-κB gene in a cell which comprises contacting the cell with an inhibitor of the interaction of amyloid-β peptide with a receptor for advanced glycation endproduct on the cell so as to inhibit the interation and thus inhibit activation of NF-κB in the cell.

The present invention also provides for a method for inhibiting periodontal disease in a subject which comprises administering topically to the subject a pharmaceutical composition which comprises sRAGE in an amount effective to accelerate wound healing and thereby inhibit periodontal disease. The pharmaceutical composition may comprise sRAGE in a toothpaste.

The present invention also provides for a method for inhibiting an advanced glycation endproduct's interaction with a receptor for advanced glycation end product when the receptor is on the surface of a cell, which comprises contacting the cell with an amount of an inhibitor of said interaction effective to inhibit interaction of the advanced glycation endproduct with the receptor for advanced glycation endproduct. The cell may be an endothelial cell, a vascular smooth muscle cell, a neuronal cell, a macrophage, a lymphocyte, a retinal vacular cell, a retinal neuronal cell, a cell associated with gingiva, a cell associated with skin, a mesangial cell or a connective tissue cell. The advanced glycation endproduct (AGE) may be a pentosidine, a carboxymethyllysine, a carboxyethyllysine, a pyrallines, an imidizalone, a methylglyoxal, an ethylglyoxal.

The present invention also provides for a method for treating a subject with a condition associated with an interaction of an advanced glycation endproduct with a receptor for advanced glycation end product on a cell, which comprises administering to the subject an inhibitor capable of inhibiting the interaction of the advanced glycation endproduct with the receptor for advanced glycation end product, the inhibitor being present in an amount effective to inhibit the advanced glycation endproduct interaction with the receptor, thereby treating the subject.

The condition may be associated with diabetes. The condition may be diabetes, renal failure, hyperlipidemic atherosclerosis, associated with diabetes, neuronal cytotoxicity, Down's syndrome, dementia associated with head trauma, amyotrophic lateral sclerosis, multiple sclerosis, amyloidosis, an autoimmune disease, inflammation, a tumor, cancer, male impotence, wound healing, periodontal disease, neuopathy, retinopathy, nephropathy or neuronal degeneration. The advanced glycation endproduct (AGE) may be a pentosidine, a carboxymethyllysine, a carboxyethyllysine, a pyrallines, an imidizalone, a methylglyoxal, an ethylglyoxal.

The agent or inhibitor of the present invention may comprise a peptide having an amino acid sequence corresponding to amino acid numbers 1-30 of the V-domain of sRAGE (soluble receptor for advanced glycation endproducts). The sRAGE may be human, mouse, rat or bovine sRAGE. The agent of the present invention may be an inhibitor. The agent may consist of amino acid numbers 1-30 of the V-domain of sRAGE. The agent may consist of amino acid numbers 1-112, which comprises the V-domain of a RAGE protein. The agent may comprise a peptide having an amino acid sequence corresponding to the amino acid sequence of a V-domain of a sRAGE linked to a second peptide, wherein the second peptide may be an albumin, a globulin or a peptide chosen from a group of peptides, wherein each peptide of the group comprises a different length peptide, and wherein the sequence of each peptide corresponds to any sequence of amino acids taken from within amino acid number 31 through amino acid number 281 of the human, bovine, mouse or rat sRAGE protien.

In the present invention the cell may be a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, or a stem cell. The present invention may also include cells of other types not explicitly listed herein. The cell may be any cell in a subject. The cell may be under oxidant stress.

The agent may be a peptide, a peptidomimetic, a nucleic acid or a small molecule. The terms "peptide" and "polypeptide" are used interchangably throughout. The peptide may be at least a portion of the sequence from amino acid 1 to amino acid 30 of sRAGE. The peptide may be a peptide consisting essentially of the amino acid sequence of Sequence I.D. No. 1, 2, 3, 4 or 5. The peptide may be smaller than Seq. I.D. Nos 1 or 2, retaining amino acid regions necessary to mimic the binding site of sRAGE. The peptide may comprise amino acids 1-112 of a RAGE protein. The peptide may consist essentially of the V-domain of a RAGE proein.

The agent may be conjugated to a carrier. The peptide or agent may be linked to an antibody, such as a Fab or a Fc fragment for specifically targeted delivery.

The agent may be a soluble V-domain of receptor for advanced glycation end product. The agent may be capable of specifically binding to the amyloid-$\beta$ peptide. The agent may bind to the amyloid-$\beta$ peptide at the site where the receptor for advanced glycation end product interacts. The agent may be a soluble extracellular portion of a receptor for advanced glycation end product, an antibody or portion thereof, wherein the antibody is capable of specifically binding to the receptor for advanced glycation endproduct. The antibody may be a monoclonal antibody or a polyclonal antibody. A portion of the antibody may be a Fab or a complementarity determining region or a variable region.

In one embodiment of the invention, the peptide may comprise at least a portion of naturally occuring soluble receptor for advanced glycation endproduct. The peptide may comprise a "V" domain of naturally occuring soluble receptor for advanced glycation endproduct. The peptide may comprise amino acids 1-30 of the V-domain or any amino acid sequence of the V-domain of naturally occuring soluble receptor for advanced glycation endproduct. The peptide may be soluble V-domain of sRAGE. The peptide may be soluble V-domain of sRAGE.

The polypeptide may be a peptidomimetic, a synthetic polypeptide or a polypeptide analog. The polypeptide may be a non-natural polypeptide which has chirality not found in nature, i.e. D-amino acids or L-amino acids.

The polypeptide may be a derivative of a natural polypeptide, a modified polypeptide, a labelled polypeptide, or a polypeptide which includes non-natural peptides. The peptidomimetic may be identified from screening large libraries of different compounds which are peptidomimetics to determine a compound which is capable of inhibiting interaction of an amyloid $\beta$ peptide with a receptor for advanced glycation endproduct.

The peptide or polypeptide of the present invention may comprise alterations to the sequences provided in Sequence I.D. Nos 1-5. The peptide of the present invention may comprise alterations in sequence which do not affect the functionality of the peptide in a negative way, but which may increase the functionality of the peptide in a position way, e.g. increase the potency of the peptide. Some examples of such alterations to the human sequence of the first 30 amino acids (1-30) of the V-domain of sRAGE (SEQ ID No: 1) are listed hereinbelow as examples:

(a) Substitute D-alanine for L-alanine in position 6;
(b) Substitue D-lysine for L-lysine in position 15;
(c) Substitute D-alanine for L-alanine in position 6 and D-lysine for L-lysine in position 15;
(d) Omit amino acids 1-5 of the V domain, making the N-amino end group L-alanine;

(e) Omit amino acids 1-5 of the V domain making the N-amino acid D-alanine;

(f) Substitute D-lysine for the L-lysine in the amino acid number "30" position of the V domain of Sequence I.D. No. 1;

(g) Substitute L-arginine for L-lysine in the 30 position of the V domain;

(h) Substitute L-arginine for L-lysine in the 30 position of the V domain and add glycine as the carboxyl terminal group to produce a 31 amino acid peptide;

(i) Substitute L-arginine for L-lysine in the 30 position of the amino acid peptide containing the amino acid sequence of 6-30 described for the V domaine of sRAGE;

(j) Substitute L-arginine for L-lysine in the 30 position of the amino acid peptide containing the amino acid sequence of 6-30 described for the V domaine of sRAGE and add glycine as the carboxyl terminal group to produce a 25 amino acid sequence peptide;

(k) Substitute D-lysine for L-lysine in the 30 position of the 6-30 amino acid sequence designated for the V domain;

(l) Substitute D-lysine for L-lysine in the 30 position of the 6-30 amino acid sequence designated for the V domaine and add L-alanine at the C-terminal position of the new 26 amino acid peptide;

(m) Substitute D-valine for L-valine in the 13 position of the V domaine 30 amino acid peptide designated 6-30 of the sRAGE V domain;

(n) Substitute D-valine for L-valine in the 13 position of the 25 amino acid peptide designated 6-30 of the sRAGE V domain;

(o) Substitute D-alanine for L-alanine in the 6 position of the 30 amino acid peptide and D-valine for L-valine in the 13 position of the 30 amino acid of the V domain;

(p) Substitute D-alanine for L-alanine in the 6 position and D-valine for L-valine in the 13 position of the 25 amino acid peptide designated 6-30 of the V domain of sRAGE;

(q) the above-listed (a)-(p) peptides derivatized through the carboxylic acid of position 30 with albumin, globulins or different length peptides composed of amino acids contained within positions 31 through 281 of the human, mouse, rat or bovine sRAGE protein.

In addition to naturally-occurring forms of polypeptides derived from sRAGE, the present invention also embraces other polypeptides such as polypeptide analogs of sRAGE which have the equivalent funcationality of the peptide of Sequence I.D. No. 1 or a more potent or more positive functionality. Such analogs include fragments of sRAGE. Following the procedures of the published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of sRAGE polypeptide. Such products share at least one of the biological properties of sRAGE but may differ in others. As examples, products of the invention include those which are foreshortened by e.g., deletions; or those which are more stable to hydrolysis (and, therefore, may have more pronounced or longerlasting effects than naturally-occurring); or which have been altered to delete or to add one or more potential sites for O-glycosylation and/or N-glycosylation or which have one or more cysteine residues deleted or replaced by e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within sRAGE, which fragments may possess one property of sRAGE and not others. It is noteworthy that activity is not necessary for any one or more of the polypeptides of the invention to have therapeutic utility or utility in other contexts, such as in assays of sRAGE antagonism. Competitive antagonists may be quite useful in, for example, cases of overproduction of sRAGE.

Of of applicability to polypeptide analogs of the invention are reports of the immunological property of synthetic peptides which substantially duplicate the amino acid sequence in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals [Lerner et al., 1981; Ross et al., 1981; Walter et al., 1981; Wong et al., 1982; Baron et al., 1982; Dressman et al., 1982; and Lerner, Scientific American, 1983. See also, Kaiser et al., 1984] relating to biological and immunological properties of synthetic peptides which approximately share secondary structures of peptide hormones but may not share their primary structural conformation.

The polypeptide of the present invention may be a peptidomimetic compound which may be at least partially unnatural. The peptidomimetic compound may be a small molecule mimic of a portion of the amino acid sequence of sRAGE. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared. The compound of the present invention may include L-,D-, DL- or unnatural amino acids, alpha, alpha-disubstituted amino acids, N-alkyl amino acids, lactic acid (an isoelectronic analog of alanine). The peptide backbone of the compound may have at least one bond replaced with PSI-[CH=CH] (Kempf et al. 1991). The compound may further include trifluorotyrosine, p-Cl-phenylalanine, p-Br-phenylalanine, poly-L-propargylglycine, poly-D,L-allyl glycine, or poly-L-allyl glycine.

One embodiment of the present invention is a peptidomimetic compound having the biological activity of preventing accelerated athersclerosis in a subject wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc- N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

In accordance with the method of this invention, the agent may comprise a peptide, a peptidomimetic, an organic molecule, a carbohydrate, a lipid, an antibody or a nucleic acid. The peptide of this invention may comprise an advanced glycation endproduct peptide or a portion thereof, a receptor for advanced glycation endproduct peptide or a portion thereof, a soluble receptor for advanced glycation endproduct peptide or a portion thereof. The peptide of the present invention may comprise any part of the first 112 amino acids of the sRAGE protein. The peptide of the present invention may comprise the V-domain of a soluble RAGE protein. The peptide of the present invention may be a smaller portion of the V-domain of a soluble RAGE protein. The peptide of the present invention may be a peptide which corresponds to the V-domain of human RAGE, mouse RAGE, rat RAGE, bovine RAGE or fish RAGE.

In accordance with the method of this invention, the agent may be a peptide (polypeptide), a peptidomimetic, an organic molecule, a carbohydrate, a lipid, an antibody or a nucleic acid. In the case of polypeptides, the polypeptide may be an advanced glycation endproduct (AGE) polypeptide or a portion thereof, a receptor for advanced glycation endproduct polypeptide or a portion thereof, a soluble receptor for advanced glycation endproduct polypeptide or a portion thereof, e.g., soluble RAGE, or a recombinant polypeptide. The polypeptide may be the V-domain of sRAGE, or amino acids 1-30 of the V-domain of sRAGE. The polypeptide of this invention may comprise an advanced glycation endproduct polypeptide or a portion thereof, a receptor for advanced glycation endproduct polypeptide or a portion thereof, a soluble receptor for advanced glycation endproduct polypeptide or a portion thereof. The polypeptide of the present invention may comprise any part of the first 112 amino acids of the sRAGE protein. The polypeptide of the present invention may comprise the V-domain of a soluble RAGE protein. The polypeptide of the present invention may be a smaller portion of the V-domain of a soluble RAGE protein. The polypeptide of the present invention may be a polypeptide which corresponds to the V-domain of human RAGE, mouse RAGE, rat RAGE, bovine RAGE or fish RAGE. The polypeptide may be synthesized chemically or produced by standard recombinant DNA methods. In the case of antibodies, the antibody may be an anti-RAGE antibody or an anti-RAGE F(ab')$_2$ fragment.

One embodiment of this invention is a method for inhibiting degeneration of a neuronal cell which includes contacting the cell with an agent comprising the V-domain of sRAGE or a portion thereof, which is capable of inhibiting interaction of an amyloid-β peptide with a receptor for advanced glycation end product on the surface of the neuronal cell.

Another embodiment of this invention is a method for inhibiting formation of an amyloid-β peptide fibril on a cell which includes contacting the cell with an agent capable of inhibiting interaction of an amyloid-β peptide with a receptor for advanced glycation end product on the surface of the cell. In one embodiment, the agent comprises amino acid numbers 1-30 of the V-domain of sRAGE.

Another embodiment of this invention is a method for inhibiting extracellular assembly of an amyloid-β peptide into a fibril which includes contacting the amyloid-β peptide with an agent capable of inhibiting interaction of an amyloid-β peptide with another amyloid-β peptide.

Another embodiment of this invention is a method for inhibiting aggregation of amyloid-β peptide on the surface of a cell which includes contacting the amyloid-β peptide with an agent capable of inhibiting interaction of the amyloid-β peptide with a receptor for advanced glycation end product.

Another embodiment of this invention is a method for inhibiting aggregation of amyloid-β peptide on the surface of a cell which includes contacting the receptor for advanced glycation end product with an agent capable of inhibiting interaction of the amyloid-β peptide with the receptor for advanced glycation end product.

Another embodiment of this invention is a method for inhibiting infiltration of a microglial cell into senile plaques which includes contacting the microglial cell with an agent capable of inhibiting interaction of an amyloid-β peptide with a receptor for advanced glycation end product on the surface of the microglial cell.

Another embodiment of this invention is a method for inhibiting activation of a microglial cell by an amyloid-β peptide which includes contacting the microglial cell with an agent capable of inhibiting interaction of the amyloid-β peptide with a receptor for advanced glycation end product on the surface of the microglial cell. The inhibition of activation may include decreased production of cytokines by the microglial cell. The interaction may be binding of the amyloid-β peptide to the receptor for advanced glycation end product on the surface of the cell.

One embodiment of this invention is a method for treating a subject with a condition associated with interaction of an amyloid-β peptide with a receptor for advanced glycation end product on a cell, which comprises administering to the subject an agent capable of inhibiting the interaction of the amyloid-β peptide with the receptor for advanced glycation end product, the agent being present in an amount effective to inhibit the amyloid-β peptide interaction with the receptor for advanced glycation end product on the cell thereby treating the subject. The condition in this embodiment may be diabetes, Alzheimer's Disease, senility, renal failure, hyperlipidemic atherosclerosis, neuronal cytotoxicity, Down's syndrome, dementia associated with head trauma, amyotrophic lateral sclerosis, multiple sclerosis, amyloidosis, autoimmune disease, inflammation, cancer or neuronal degeneration.

The subject may be a mammal or non-mammal. The subject may be a mammal or a human. The subject may be a mouse, a cow, a monkey, a horse, a pig, or a dog. The subject may be a diabetic subject. The subject may be suffering from an apolipoprotein deficiency, or from hyperlipidemia. The hyperlipidemia may be hypercholesterolemia or hypertriglyceridemia. The subject may have a glucose metabolism disorder. The subject may be an obese subject. The subject may have genetically-mediated or diet-induced hyperlipidemia. AGEs form in lipid-enriched environments even in euglycemia. The subject may be suffering from oxidant stress. The subject may be suffering from neuronal degeneration or neurotoxicity.

In another embodiment of the present invention, the method may further comprise administering to the subject a pharmaceutically acceptable carrier during the administration of the agent. The administration may comprise intralesional, intraperitoneal, intramuscular or intravenous injection; infusion; liposome-mediated delivery; or topical, nasal, oral, ocular or otic delivery. The agent may be linked to a pharmaceutically acceptable carrier.

The agent may be delivered hourly, daily, weekly, monthly, yearly (e.g. in a time release form) or as a one time delivery. The delivery may be continuous delivery for a period of time, e.g. intravenous delivery. The agent or pharmaceutical composition of the present invention may be delivered intercranially or into the spinal fluid.

The effective amount of the agent may comprise from about 0.000001 mg/kg body weight to about 100 mg/kg body weight. In one embodiment, the effective amount may comprise from about 0.001 mg/kg body weight to about 50 mg/kg body weight. In another embodiment, the effective amount may range from about 0.01 mg/kg body weight to about 10 mg/kg body weight. The actual effective amount will be based upon the size of the agent, the biodegradability of the agent, the bioactivity of the agent and the bioavailability of the agent. The agent may be delivered topically in a creme or salve carrier. It may be reapplied as needed based upon the absorbancy of the carrier to the skin or mucosa or wound. If the agent does not degrade quickly, is bioavailable and highly active, a smaller amount will be required to be effective. The effective amount will be known to one of skill in the art; it will also be dependent upon the form of the agent, the size of the agent and the bioactivity of the agent. One of skill in the art could routinely perform empirical activity tests for a agent to determine the bioactivity in bioassays and thus determine the effective amount.

In this embodiment, the condition may be associated with degeneration of a neuronal cell in the subject, with formation of an amyloid-β peptide fibril, with aggregation of amyloid-β peptide, with infiltration of a microglial cell into a senile plaque, or with activation of a microglial cell by an amyloid-β peptide, wherein the activation comprises production of cytokines by the microglial cell. Another embodiment of this invention is a method for evaluating the ability of an agent to inhibit binding of an amyloid-β peptide with a receptor for advanced glycation end product on the surface of a cell which includes: a) contacting the cell with the agent and amyloid-β peptide; b) determining the amount of amyloid-β peptide bound to the cell and c) comparing the amount of bound amyloid-β peptide determined in step b) with the amount determined in the absence of the agent, thus evaluating the ability of the agent to inhibit the binding of amyloid-β peptide to the receptor for advanced glycation end product on the surface of the cell.

In this embodiment, the cell may be contacted with the agent and the amyloid-β peptide simultaneously or the cell may be contacted with the amyloid-β peptide and the agent. The agent may be capable of specifically binding to the amyloid-β peptide. The agent may bind to amyloid-β peptide at the site where the receptor for advanced glycation end product interacts. The agent may be a soluble extracellular portion of a receptor for advanced glycation end product. The agent may be bound to a solid support. The agent may be expressed on the surface of a cell.

Another embodiment of this invention is a method for inhibiting activation of an NF-κB gene in a cell which comprises contacting the cell with an agent which is capable of inhibiting interaction of amyloid-β peptide with a receptor for advanced glycation endproduct on the cell, thus inhibiting activation of NF-κB in the cell.

The present invention provides for a pharmaceutical composition which comprises an agent capable of inhibiting interaction of amyloid-β peptide with a receptor for advanced glycation endproduct and a pharmaceutically acceptable carrier. The carrier may be a diluent, an aerosol, a topical carrier, an aquous solution, a nonaqueous solution or a solid carrier.

As used herein, the term "oxidant stress" encompasses the perturbation of the ability of a cell to ameliorate the toxic effects of oxidants. Oxidants may include hydrogen peroxide or oxygen radicals that are capable of reacting with bases in the cell including DNA. A cell under "oxidant stress" may undergo biochemical, metabolic, physiological and/or chemical modifications to counter the introduction of such oxidants. Such modifications may include lipid peroxidation, NF-κB activation, heme oxygenase type I induction and DNA mutagenesis. Also, antioxidants such as glutathione are capable of lowering the effects of oxidants. The present invention provides agents and pharmaceutical compositions which are capable of inhibiting the effects of oxidant stress upon a cell. The invention also provides methods for ameliorating the symptoms of oxidant stress in a subject which comprises administering to the subject an amount of the agent or pharmaceutical composition effective to inhibit oxidant stress and thereby ameliorate the symptoms of oxidant stress in the subject.

As used herein, the term "neurotoxicity" encompasses the negative metabolic, biochemical and physiological effects on a neuronal cell which may result in a debilitation of the neuronal celluar functions. Such functions may include memory, learning, perception, neuronal electrophysiology (i.e. action potentials, polarizations and synapses), synapse formation, both chemical and electrical, channel functions, neurotransmitter release and detection and neuromotor functions. Neurotoxicity may include neuronal cytotoxicity.

As used herein, the term "neuronal degeneration" encompasses a decline in normal functioning of a neuronal cell. Such a decline may include a decline in memory, learning, perception, neuronal electrophysiology (i.e. action potentials, polarizations and synapses), synapse formation, both chemical and electrical, channel functions, neurotransmitter release and detection and neuromotor functions.

In the practice of any of the methods of the invention or preparation of any of the pharmaceutical compositions a "therapeutically effective amount" is an amount which is capable of inhibiting the binding of an amyloid-β peptide with a receptor for advanced glycation endproduct. Accordingly, the effective amount will vary with the subject being treated, as well as the condition to be treated.

As used herein, the term "suitable pharmaceutically acceptable carrier" encompasses any of the standard pharmaceutically accepted carriers, such as phosphate buffered saline solution, acetate buffered saline solution (a likely vehicle for parenteral administration), water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

When administered orally or topically, such agents and pharmaceutical compositions would be delivered using different carriers. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. The specific carrier would need to be selected based upon the desired method of deliver, e.g., PBS could be used for intravenous or systemic delivery and vegetable fats, creams, salves, ointments or gels may be used for topical delivery.

This invention also provides for pharmaceutical compositions including therapeutically effective amounts of protein compositions and/or agents capable of inhibiting the binding of an amyloid-β peptide with a receptor for advanced glycation endproduct in the subject of the invention together with suitable diluents, preservatives, solubilizers, emulsifiers, adjuvants and/or carriers useful in treatment of neuronal degradation due to aging, a learning disability, or a neurological disorder. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the agent, complexation with metal ions, or incorporation of the agent into or onto particulate preparations of polymeric agents such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the agent or composition. The choice of compositions will depend on the physical and chemical properties of the agent capable of alleviating the symptoms of the cognitive disorder of memory or the learning disability in the subject.

The agent of the present invention may be delivered locally via a capsule which allows sustained release of the agent or the peptide over a period of time. Controlled or sustained release compositions include formulation in lipophilic depots (e.g., fatty acids, waxes, oils). Also comprehended by the invention are particulate compositions coated with polymers (e.g., poloxamers or poloxamines) and the agent coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the agent of the invention may be "labeled" by association with a detectable marker substance (e.g., radiolabeled with $^{125}$I or biotinylated) to provide reagents useful in detection and quantification of compound or its receptor bearing cells or its derivatives in solid tissue and fluid samples such as blood, cerebral spinal fluid or urine.

When administered, agents (such as a peptide comprising the V-domain of sRAGE) are often cleared rapidly from the circulation and may therefore elicit relatively short-lived pharmacological activity. Consequently, frequent injections of relatively large doses of bioactive agents may by required to sustain therapeutic efficacy. Agents modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified agents (Abuchowski et al., 1981; Newmark et al., 1982; and Katre et al., 1987). Such modifications may also increase the agent's solubility in aqueous solution, eliminate aggregation, enhance the physical and chemical stability of the agent, and greatly reduce the immunogenicity and reactivity of the agent. As a result, the desired in vivo biological activity may be achieved by the administration of such polymer-agent adducts less frequently or in lower doses than with the unmodified agent.

Attachment of polyethylene glycol (PEG) to agents is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the agent or against cells which may produce the compound. The agent of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

Wound Healing

The peptides and agents of the present invention may be used to treat wound healing in subjects. The wound healing may be associated with various diseases or conditions. The diseases or conditions may impair normal wound healing or contribute to the existence of wounds which require healing. The subjects may be treated with the peptides or agents or pharmaceutical compositions of the present invention in order to treat slow healing, recalcitrant periodontal disease, wound healing impairment due to diabetes and wound healing impairments due to autoimmune disease. The present invention provides compounds and pharmaceutical compositions useful for treating impaired wound healing resultant from aging. The effect of topical administration of the agent can be enhanced by parenteral administration of the active ingredient in a pharmaceutically acceptable dosage form.

Neurologic Disease

The pathologic hallmarks of Alzheimer's disease (AD) are intracellular and extracellular deposition of filamentous proteins which closely correlates with eventual neuronal dysfunction and clinical dementia (for reviews see Goedert, 1993; Haass et al., 1994; Kosik, 1994; Trojanowski et al., 1994; Wischik, 1989). Amyloid-β peptide (Aβ) is the principal component of extracellular deposits in AD, both in senile/diffuse plaques and in cerebral vasculature. Aβ has been shown to promote neurite outgrowth, generate reactive oxygen intermediates (ROIs), induce cellular oxidant stress, lead to neuronal cytotoxicity, and promote microglial activation (Behl et al., 1994; Davis et al., 1992; Hensley, et al., 1994; Koh, et al., 1990; Koo et al., 1993; Loo et al., 1993; Meda et al., 1995; Pike et al., 1993; Yankner et al., 1990). For Aβ to induce these multiple cellular effects, it is likely that plasma membranes present a binding protein(s) which engages Aβ. In this context, several cell-associated proteins, as well as sulfated proteoglycans, can interact with Aβ. These include: substance P receptor, the serpin-enzyme complex (SEC) receptor, apolipoprotein E, apolipoprotein J (clusterin) transthyretin, alpha-1 anti-chymotrypsin, β-amyloid precursor protein, and sulphonates/heparan sulfates (Abraham et al., 1988; Fraser et al., 1992; Fraser et al., 1993; Ghiso et al., 1993; Joslin et al., 1991; Kimura et al., 1993; Kisilevsky et al., 1995; Strittmatter et al., 1993a; Strittmatter et al., 1993b; Schwarzman et al., 1994; Snow et al., 1994; Yankner et al., 1990). Of these, the substance P receptor and SEC receptor might function as neuronal cell surface receptors for Aβ, though direct evidence for this is lacking (Fraser et al., 1993; Joslin et al., 1991; Kimura et al., 1993; Yankner et al., 1990). In fact, the role of substance P receptors is controversial, and it is not known whether Aβ alone interacts with the receptor, or if costimulators are required (Calligaro et al., 1993; Kimura et al., 1993; Mitsuhashi et al., 1991) and the SEC receptor has yet to be fully characterized.

CLINICAL ASPECTS

In certain embodiments of the present invention, the subject may be suffering from clinical aspects as described hereinbelow and as further described in Harper's Biochemistry, R. K. Murray, et al. (Editors) 21st Edition, (1988) Appelton & Lange, East Norwalk, Conn. Such clinical aspects may predispose the subject to atherosclerosis or to accelerated atherosclerosis. Thus, such subjects would benefit from the administration of a polypeptide derived from sRAGE in an effective amount over an effective time.

The subject of the present invention may demonstrate clinical signs of atherosclerosis, hypercholesterolemia or other disorders as discussed hereinbelow.

Clinically, hypercholesterolemia may be treated by interrupting the enterohepatic circulation of bile acids. It is reported that significant reductions of plasma cholesterol can be effected by this procedure, which can be accomplished by the use of cholestyramine resin or surgically by the ileal exclusion operations. Both procedures cause a block in the reabsorption of bile acids. Then, because of release from feedback regulation normally exerted by bile acids, the conversion of cholesterol to bile acids is greatly enhanced in an effort to maintain the pool of bile acids. LDL (low density lipoprotein) receptors in the liver are up-regulated, causing increased uptake of LDL with consequent lowering of plasma cholesterol.

Cholesterol, Atherosclerosis, and Coronary Heart Disease

The peptides, agents and pharmaceutical compositions of the present invention may be used as therapeutic agents to inhibit symptoms of diseases in a subject associated with cholesterol metabolism, atherosclerosis or coronary heart disease. Some symptoms of such diseases which may be inhibited or ameliorated or prevented through the administration of the agents and pharmaceutical compositions of the present invention are discussed hereinbelow. For example, the agents and pharmaceutical compositions of the present invention may be administered to a subject suffering from symptoms of coronary heart disease in order to protect the integrity of the endothelial cells of the subject and thereby inhibit the symptoms of the coronary heart disease.

Many investigators have demonstrated a correlation between raised serum lipid levels and the incidence of coronary heart disease and atherosclerosis in humans. Of the serum lipids, cholesterol has been the one most often singled out as being chiefly concerned in the relationship. However, other parameters such as serum triacylglycerol concentration show similar correlations. Patients with arterial disease can have any one of the following abnormalities: (1) elevated concentrations of VLDL (very low density lipoproteins) with normal concentrations of LDL; (2) elevated LDL with Normal VLDL; (3) elevation of both lipoprotein fractions. There is also an inverse relationship between HDL (high density lipoproteins)($HDL_2$) concentrations and coronary heart disease, and some consider that the most predictive relationship is the LDL:HDL cholesterol ratio. This relationship is explainable in terms of the proposed roles of LDL in transporting cholesterol to the tissues and of HDL acting as the scavenger of cholesterol.

Atherosclerosis is characterized by the deposition of cholesterol and cholesteryl ester of lipoproteins containing apo-B-100 in the connective tissue of the arterial walls. Diseases in which prolonged elevated levels of VLDL, IDL, or LDL occur in the blood (e.g., diabetes, mellitus, lipid nephrosis, hypothyroidism, and other conditions of hyperlipidemia) are often accompanied by premature or more sever atherosclerosis.

Experiments on the induction of atherosclerosis in animals indicate a wide species variation in susceptibility. The rabbit, pig, monkey, and humans are species in which atherosclerosis can be induced by feeding cholesterol. The rat, dog, mouse and cat are resistant. Thyroidectomy or treatment with thiouracil drugs will allow induction of atherosclerosis in the dog and rat. Low blood cholesterol is a characteristic of hyperthyroidism.

Hereditary factors play the greatest role in determining individual blood cholesterol concentrations, but of the dietary and environmental factors that lower blood cholesterol, the substitution in the diet of polyunsaturated fatty acids for some of the saturated fatty acids has been the most intensely studied.

Naturally occurring oils that contain a high proportion of linoleic acid are beneficial in lowering plasma cholesterol and include peanut, cottonseed, corn, and soybean oil whereas butterfat, beef fat, and coconut oil, containing a high proportion of saturated fatty acids, raise the level. Sucrose and fructose have a greater effect in raising blood lipids, particularly triacylglycerols, than do other carbohydrates.

The reason for the cholesterol-lowering effect of polyunsaturated fatty acids is still not clear. However, several hypotheses have been advanced to explain the effect, including the stimulation of cholesterol excretion into the intestine and the stimulation of the oxidation of cholesterol to bile acids. It is possible that cholesteryl esters of polyunsaturated fatty acids are more rapidly metabolized by the liver and other tissues, which might enhance their rate of turnover and excretion. There is other evidence that the effect if largely due to a shift in distribution of cholesterol from the plasma into the tissues because of increased catabolic rate of LDL. Saturated fatty acids cause the formation of smaller VLDL particles that contain relatively more cholesterol, and they are utilized by extrahepatic tissues at a slower rate than are larger particles. All of these tendencies may be regarded as atherogenic.

Additional factors considered to play a part in coronary heart disease include high blood pressure, smoking, obesity, lack of exercise, and drinking soft as opposed to hard water. Elevation of plasma free fatty acids will also lead to increase VLDL secretion by the liver, involving extra triacylglycerol and cholesterol output into the circulation. Factors leading to higher or fluctuating levels of free fatty acids include emotional stress, nicotine from cigarette smoking, coffee drinking, and partaking of a few large meals rather than more continuous feeding. Premenopausal women appear to be protected against many of these deleterious factors, possibly because they have higher concentrations of HDL than do men and postmenopausal women.

Hypolipidemic Drugs

When dietary measures fail to achieve reduced serum lipid levels, the use of hypolipidemic drugs may be resorted to. Such drugs may be used in conjunction with the agents and pharmaceutical compositions of the present invention, i.e., such drugs may be administered to a subject along with the agents of the present invention. Several drugs are known to block the formation of cholesterol at various stages in the biosynthetic pathway. Many of these drugs have harmful effects, but the fungal inhibitors of HMG-COA reductase, compactin and mevinolin, reduce LDL cholesterol levels with few adverse effects. Sitosterol is a hypocholesterolemic agent that acts by blocking the absorption of cholesterol in the gastrointestinal tract. Resins such as colestipol and cholestyramine (Questran) prevent the reabsorption of bile salts by combining with them, thereby increasing their fecal loss. Neomycin also inhibits reabsorption of bile salts. Clofibrate and gembivrozil exert at least part of their hypolipidemic effect by diverting the hepatic flow of free fatty acids from the pathways of esterification into those of oxidation, thus decreasing the secretion of triacylglycerol and cholesterol containing VLDL by the liver. In addition, they facilitate hydrolysis of VLDL triacylglycerols by lipoprotein lipase. Probucol appears to increase LDL catabolism via receptor-independent pathways. Nicotinic acid reduces the flux of FFA by inhibiting adipose tissue lipolysis, thereby inhibiting VLDL production by the liver.

Disorders of the Plasma Lipoproteins (Dyslipoproteinemias)

A few individuals in the population exhibit inherited defects in their lipoproteins, leading to the primary condition of whether hypo- or hyperlipoproteinemia. Many others having defects such as diabetes mellitus, hypothyroidism, and atherosclerosis show abnormal lipoprotein patterns that are very similar to one or another of the primary inherited conditions. Virtually all of these primary conditions are due to a defect at one or another stage in the course of lipoprotein formation, transport, or destruction. Not all of the abnormalities are harmful.

Hypolipoproteinemia

1. Abetalipoproteinemia—This is a rare inherited disease characterized by absence of β-lipoprotein (LDL) in plasma. The blood lipids are present in low concentrations—especially acylglycerols, which are virtually absent, since no chylomicrons or VLDL are formed. Both the intestine and the liver accumulate acylglycerols. Abetalipoproteinemia is due to a defect in apoprotein B synthesis.

2. Familial hypobetalipoproteinemia—In hypobetalipoproteinemia, LDL concentration is between 10 and 50% of normal, but chylomicron formation occurs. It must be concluded that apo-B is essential for triacylglycerol transport. Most individuals are healthy and long-lived.

3. Familial alpha-lipoprotein deficiency (Tangier disease)—In the homozygous individual, there is near absence of plasma HDL and accumulation of cholesteryl esters in the tissues. There is no impairment of chylomicron formation or secretion of VLDL by the liver. However, on electrophoresis, there is no pre-β-lipoprotein, but a broad β-band is found containing the endogenous triacylglycerol. This is because the normal pre-β-band contains other apoproteins normally provided by HDL. Patients tend to develop hypertriacylglycerolemia as a result of the absence of apo-C-II, which normally activates lipoprotein lipase.

Hyperlipoproteinemia

1. Familial lipoprotein lipase deficiency (type I)—This condition is characterized by very slow clearing of chylomicrons from the circulation, leading to abnormally raised levels of chylomicrons. VLDL may be raised, but there is a decrease in LDL and HDL. Thus, the condition is fat-induced. It may be corrected by reducing the quantity of fat and increasing the proportion of complex carbohydrate in the diet. A variation of this disease is caused by a deficiency in apo-C-II, required as a cofactor for lipoprotein lipase.

2. Familial hypercholesterolemia (type II)—Patients are characterized by hyperbetalipoproteinemia (LDL), which is associated with increased plasma total cholesterol. There may also be a tendency for the VLDL to be elevated in type IIb. Therefore, the patient may have somewhat elevated triacylglycerol levels but the plasma—as is not true in the other types of hyperlipoproteinemia—remains clear. Lipid deposition in the tissue (e.g., xanthomas, atheromas) is common. A type II pattern may also arise as a secondary result of hypothyroidism. The disease appears to be associated with reduced rates of clearance of LDL from the circulation due to defective LDL receptors and is associated with an increased incidence of atherosclerosis. Reduction of dietary cholesterol and saturated fats may be of use in treatment. A disease producing hypercholesterolemia but due to a different cause is Wolman's disease (cholesteryl ester storage disease). This is due to a deficiency of cholesteryl ester hydrolase in lysosomes of cells such as fibroblasts that normally metabolize LDL.

3. Familial type III hyperlipoproteinemia (broad beta disease, remnant removal disease, familial dysbetalipoproteinemia)—This condition is characterized by an increase in both chylomicron and VLDL remnant; these are lipoproteins of density less than 1.019 but appear as a broad β-band on electrophoresis (β-VLDL). They cause hypercholesterolemia and hypertriacylglycerolemia. Xanthomas and atherosclerosis of both peripheral and coronary arteries are present. Treatment by weight reduction and diets containing complex carbohydrates, unsaturated fats, and little cholesterol is recommended. The disease is due to a deficiency in remnant metabolism by the liver caused by an abnormality in apo-E, which is normally present in 3 isoforms, E2, E3, and E4. Patients with type III hyperlipoproteinemia possess only E2, which does not react with the E receptor.

4. Familial hypertriacylglycerolemia (type IV)—This condition is characterized by high levels of endogenously produced triacylglycerol (VLDL). Cholesterol levels rise in proportion to the hypertriacylglycerolemia, and glucose intolerance is frequently present. Both LDL and HDL are subnormal in quantity. This lipoprotein pattern is also commonly associated with coronary heart disease, type II non-insulin-dependent diabetes mellitus, obesity, and many other conditions, including alcoholism and the taking of progestational hormones. Treatment of primary type IV hyperlipoproteinemia is by weight reduction; replacement of soluble diet carbohydrate with complex carbohydrate, unsaturated fat, low-cholesterol diets; and also hypolipidemic agents.

5. Familial type V hyperlipoproteinemia—The lipoprotein pattern is complex, since both chylomicrons and VLDL are elevated, causing both triacylglycerolemia and cholesterolemia. Concentrations of LDL and HDL are low. Xanthomas are frequently present, but the incidence of atherosclerosis is apparently not striking. Glucose tolerance is abnormal and frequently associated with obesity and diabetes. The reason for the condition, which is familial, is not clear. Treatment has consisted of weight reduction followed by a diet not too high in either carbohydrate or fat.

It has been suggested that a further cause of hypolipoproteinemia is overproduction of apo-B, which can influence plasma concentrations of VLDL and LDL.

6. Familial hyperalphalipoproteinemia—This is a rare condition associated with increased concentrations of HDL apparently beneficial to health.

Familial Lecithin: Cholesterol Acyltransferase (LCAT) Deficiency: In affected subjects, the plasma concentration of cholesteryl esters and lysolecithin is low, whereas the concentration of cholesterol and lecithin is raised. The plasma tends to be turbid. Abnormalities are also found in the lipoproteins. One HDL fraction contains disk-shaped structures in stacks or rouleaux that are clearly nascent HDL unable to take up cholesterol owing to the absence of LCAT. Also present as an abnormal LDL subfraction is lipoprotein-X, otherwise found only in patients with cholestasis. VLDL are also abnormal, migrating as β-lipoproteins upon electrophoresis (β-VLDL). Patients with parenchymal liver disease also show a decrease of LCAT activity and abnormalities in the serum lipids and lipoproteins.

Pharmaceutical Carriers

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient of the present invention (e.g., the V-domain polypeptide derived from sRAGE, or composition thereof) can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Atherosclerosis

In one embodiment of the present invention, the subject may be predisposed to atherosclerosis. This predisposition may include genetic predisposition, environmental predisposition, metabolic predisposition or physical predisposition. There have been recent reviews of atherosclerosis and cardiovascular disease. For example: Keating and Sanguinetti, (May 1996) Molecular Genetic Insights into Cardiovascular Disease, Science 272:681-685 is incorporated by reference in its entirety into the present application. The authors review the application of molecular tools to inherited forms of cardiovascular disease such as arrhythmias, cardiomyopathies, and vascular disease. Table 1 of this reference includes cardiac diseases and the aberrant protein associated with each disease. The diseases listed are: LQT disease, familial hypertrophic cardiomyopathy; duchenne and Becker muscular dystrophy; Barth syndrome Acyl-CoA dehydrogenase deficiencies; mitochondrial disorders; familial hypercholesterolemia; hypobetalipoproteinemia; homocystinuria; Type III hyperlipoproteinemia; supravalvular aortic stenosis; Ehler-Danlos syndrome IV; Marf a syndrome; Heredity hemorrhagic telangiectasia. These conditions are included as possible predispositions of a subject for atherosclerosis.

Furthermore, mouse models of atherosclerosis are reviewed in Breslow (1996) Mouse Models of Atherosclerosis, Science 272:685. This reference is also incorporated by reference in its entirety into the present application. Breslow also includes a table (Table 1) which recites various mouse models and the atherogenic stimulus. For example, mouse models include C57BL/6; Apo E deficiency; ApoE lesion; ApoE R142C; LDL receptor deficiency; and HuBTg. One embodiment of the present invention is wherein a subject has a predisposition to atherosclerosis as shown by the mouse models presented in Breslow's publication.

Gibbons and Dzau review vascular disease in Molecular Therapies for Vascular Disease, Science Vol. 272, pages 689–693. In one embodiment of the present invention, the subject may manifest the pathological events as described in Table 1 of the Gibbons and Dzau publication. For example, the subject may have endothelial dysfunction, endothelial injury, cell activation and phenotypic modulation, dysregulated cell growth, dysregulated apoptosis, thrombosis, plaque rupture, abnormal cell migration or extracellular or intracellular matrix modification.

In another embodiment of the present invention, the subject may have diabetes. The subject may demonstrate complications associated with diabetes. Some examples of such complications include activation of endothelial and macrophage AGE receptors, altered lipoproteins, matrix, and basement membrane proteins; altered contractility and hormone responsiveness of vascular smooth muscle; altered endothelial cell permeability; sorbitol accumulation; neural myoinositol depletion or altered Na-K ATPase activity. Such complications are discussed in a recent publication by Porte and Schwartz, Diabetes Complications: Why is Glucose potentially Toxic?, Science, Vol. 272, pages 699–700.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

The First 30 Amino Acids of the V-type Domain of Extracellular Soluble (sRAGE) Mediates its Interactions with Advanced Glycation Endproducts (AGEs) And Amyloid-β Peptide The extracellular domain of RAGE (Receptor for Advanced Glycation Endproducts) contains one "V"-type domain followed by two "C"-type immunoglobulin domains. This portion of the molecule, called soluble or sRAGE, mediates the interaction of Advanced Glycation Endproducts (AGEs) and amyloid-β-peptide with the cell surface receptor. sRAGE binds up AGEs or amyloid-β-peptide and interferes with the ability of these ligands to interact with, and activate, cellular RAGE on a range of cell types. In vivo, administration of sRAGE suppresses accelerated atherosclerosis in a murine model of accelerated diabetic vascular disease in apolipoprotein E null mice and ameliorates impaired wound healing in genetically-diabetic db+/db+ mice. In order to delineate which portion of sRAGE mediates these interactions with either AGEs or amyloid-β-peptide, a series of DNA constructs (including DNA coding for the V-domain, the C1-domain or the C2-domain) were generated along with a series of peptides representing sequences throughout the three domains. The data herein indicate that the ligand-binding domain for both AGEs and amyloid-β-peptide in sRAGE lies within the first 30 amino acids of the V-domain. Moreover, the data indicate that the C1-domain or the C2-domain or peptide sequences within those domains do not mediate the interaction of these ligands with sRAGE. These data indicate that the first 30 amino acids of sRAGE may represent an important target for drug identification, screening and development to treat diseases in which AGEs accumulate, such as the complications of diabetes, as well as Alzheimer's disease.

RAGE (Receptor for AGE) was first identified as a cellular interaction site for the interaction of Advanced Glycation Endproducts (AGEs), the products of irreversible nonenzymatic glycation and oxidation of proteins/lipids, which accumulate during normal aging, diabetes as well as in renal failure and amyloidoses (Ruderman et al., 1992; Baynes, 1991; Sell et al., 1989; Brownlee et al., 1988; Hicks et al., 1988). RAGE (Schmidt et al., 1992; Neeper et al., 1992) is a member of the immunoglobulin superfamily of cell surface molecules whose extracellular portion contains one "V"-type domain followed by two "C"-type immunoglobulin domains. The putative hydropathy plot further predicts that this extracellular portion is preceded by an approximately 22 amino acid leader peptide, and is followed by a putative hydrophobic transmembrane spanning domain, and lastly by a highly-charged cytosolic domain (Neeper et al., 1992). RAGE is remarkably conserved among the species examined thus far (bovine, human, mouse and rat) (Neeper et al., 1992), with greater than 90% homology observed at both the nucleic acid and amino acid levels.

RAGE as a receptor for Advanced Glycation Endproducts (AGEs). Previous studies have demonstrated that RAGE is present on cell types that are specific targets in the pathogenesis of complications in diabetes, specifically endothelial cells, vascular smooth muscle cells, macrophages, mesangial cells, vascular and neural cells of the retina, as well as neurons (in the central and peripheral nervous system) (Brett et al., 1993). In this context, the interaction of AGEs with RAGE results in a number of alterations in vascular and inflammatory cell phenotype, all of which are likely important in the pathogenesis of diabetic and aging complications (Schmidt et al., 1993; Schmidt et al., 1994; Schmidt et al., 1995; Wautier et al., 1996; Yan et al., 1994; Miyata et al., 1996; Lander et al., 1997)). For example, AGE-RAGE interaction results in enhanced migration and activation of macrophages (Schmidt et al., 1993), increased expression of Interleukin-6 in the livers of AGE-treated mice (Schmidt et al., 1994), enhanced expression of Vascular Cell Adhesion Molecule-1 by the vascular endothelium (Schmidt et al., 1995), vascular hyper-permeability (Wautier et al., 1996) and enhanced cellular oxidant stress (Yan et al., 1994, Miyata et al., 1996). A central means by which AGE-RAGE interaction imparts these effects is via activation of oxidant-sensitive pathways including $p21^{ras}$ and MAP kinases (Lander et al., 1997).

The effects of AGE-RAGE interaction are largely blocked by pretreatment of a cell culture system or live mice with an anti-RAGE compound composed of the "V" domain and two "C"-type domains (Schmidt et al., 1993; Schmidt et al., 1994; Schmidt et al., 1995; Wautier et al., 1996; Yan et al., 1994; Miyata et al., 1996; Lander et al., 1997). Furthermore, in recent studies, treatment of diabetic mice with sRAGE ameliorated impaired wound healing in a full-thickness excisional model (Wu et al., 1997) and suppressed accelerated diabetic atherosclerosis in apolipoprotein E null mice rendered diabetic with streptozotocin (Park et al., 1997).

RAGE as a receptor for amyloid-beta peptide. Amyloid-beta peptide is an important pathogenetic species in the development of neuronal toxicity in Alzheimer's disease (Yan et al., 1996). RAGE was identified as a central interaction site for amyloid-beta peptide on neurons; the interaction of which results in enhanced oxidant stress, neuronal cytotoxicity and expression of macrophage colony stimulating factor (Yan et al., 1996; Yan et al., 1997). These effects, as in the case of AGEs, are blocked in cell culture models in the presence of either anti-RAGE IgG or sRAGE (Yan et al., 1996; Yan et al., 1997).

Therefore, the purpose of the studies outlined below was to delineate the precise interaction site of AGEs and amyloid-beta peptide with sRAGE as a means of understanding how sRAGE imparts its beneficial effects. Ultimately, the results of these studies are be most useful in the development of drugs designed to treat disorders in which AGEs accumulate, such as the complications of diabetes, as well as Alzheimer's disease.

Materials. Advanced Glycation Endproducts (AGEs) were prepared as previously described (Schmidt et al., 1992; Neeper et al., 1992) using materials obtained from SIGMA®. Amyloid-beta peptide (1-42) was purchased from Quality Control Biochemicals. All peptides were prepared according to the human sequence (Neeper et al., 1992) by Quality Control Biochemicals.

Constructs. The GST-fusion protein system was utilized to prepare soluble V-domain, and soluble C1 and C2-domains according to the manufacturer's instructions (PHARMACIA®).

Binding Assays. AGE bovine serum albumin (5 μg) was loaded onto the wells of a NUNC® Maxisorp dish in sodium bicarbonate/sodium carbonate buffer (pH 9.8) overnight at 4° C. The following morning, wells were aspirated and blocked with phosphate buffered saline (with calcium/magnesium) containing bovine serum albumin (1%) for two hrs at 37° C. Wells were then washed once with phosphate buffered saline (without calcium/magnesium) containing TWEEN® 20 (20%); 0.150 ml/well. A radiological binding assay was then performed in phosphate buffered saline containing 0.2% bovine serum albumin for 2 hrs at 37° C. Utilizing radiolabeled ($^{125}$I; using Iodogen (PIERCE®)) full length soluble RAGE (100 nM; specific activity 7,000-8,000 cpm/ng) in the presence or absence of unlabeled soluble RAGE (50×molar excess) or the indicated molar excess of domain or peptide. Wells were then eluted after washing as above with buffer containing NP-40 (1%) and NaCl (0.15M). The material retrieved was then counted in a gamma counter (LKB®). In experiments with amyloid-beta peptide, amyloid-beta peptide 1-42 (5 μg) was loaded onto the wells of a NUNC® Maxisorp dish in sodium bicarbonate/sodium carbonate buffer (pH 9.8) overnight at 4° C. The following morning, wells were aspirated and blocked with phosphate buffered saline (without calcium/magnesium) containing bovine serum albumin (1%) for two hrs at 37° C. Binding assay was then performed in phosphate buffered saline containing 0.2% bovine serum albumin for 2 hrs at 37° C. utilizing radiolabeled ($^{125}$I; using Iodogen (PIERCE®)) full length soluble RAGE 950 nM; specific activity 7,000-8,000 cpm/ng) in the presence or absence of unlabeled soluble RAGE (molar excess indicated below) or the indicated molar excess of domain or peptide. Wells were then eluted after washing as above with buffer containing NP-40 (1%) and NaCl (0.15 M). The material retrieved was then counted in a gamma counter as above.

RESULTS

Interaction of AGEs with sRAGE. The first experiments sought to determine which of the three extracellular domains comprising sRAGE interacted with AGEs. Radioligand binding assays revealed that while unlabeled soluble RAGE (full-length) competed for binding of radiolabeled sRAGE with immobilized AGE by 83%, unlabeled V-domain competed 89%, while C1 and C2 domains were without effect (30% and 19% competition, respectively), when all unlabeled competitors were utilized at a 50-fold molar excess (Table 1). These data indicated that only V-domain appeared to mediate the interaction with AGEs. These effects of unlabeled V-domain were dose-dependent; at an 100-fold molar excess 80% competition was observed. This was reduced to 53% at a 12.5-fold molar excess and to no competition (0) at a 1.56-fold molar excess of unlabeled V-domain (Table II). A series of peptides was then prepared comprising different portions of the V-domain of sRAGE. These data indicated that at 50-fold molar excess, essentially no competition was obtained using the following peptides (peptides consisting of amino acid numbers of sRAGE: 1-13, 18-28, 31-60, and 46-60; Table III). Control peptides from C1 and C2 domains were also utilized (peptides consisting of amino acid numbers of sRAGE: 157-169 and 270-281, respectively) which had no effect (Table III). However, peptides consisting of amino acid numbers 1-30 and 16-30 of the V-domain did inhibit the binding of radiolabeled sRAGE to immobilized AGE. At a 50-fold molar excess, the peptide consisting of amino acid numbers 1-30 of sRAGE inhibited the binding by 78%, at a 25-fold molar excess, the peptide consisting of amino acid numbers 1-30 of sRAGE inhibited the binding by 76% and at a 1-fold molar excess there was no (0) competition (Table III). At a 50-fold molar excess, a peptide consisting of amino acid numbers 16-30 of sRAGE inhibited the binding of radiolabeled sRAGE to immobilized AGE by 73%, at a 25-fold molar excess, a peptide consisting of amino acids 16-30 of sRAGE inhibited the binding by 20% and at a 1-fold molar excess, there was no competition (Table III). Smaller peptides were than prepared (peptides consisting of amino acid numbers 1-25 and 10-25 of sRAGE) in an effort to further delineate the precise binding site. Even at a 50-fold molar excess, an unlabeled peptide consisting of amino acid numbers 1-25 of sRAGE only inhibited the binding of radiolabeled sRAGE to immobilized AGE by 31% and an unlabeled peptide consisting of amino acid numbers 10-25 of sRAGE only had a 26% competitive effect (Table III). These data suggest that the peptide consisting of amino acid numbers 1-30 of sRAGE is an effective competitor of the binding of sRAGE to immobilized AGE.

Interaction of amyloid-beta peptide with sRAGE. It was first determined which of the three extracellular domains comprising sRAGE interacted with amyloid-beta peptide. Radioligand binding assays revealed that while unlabeled soluble RAGE (full-length) competed for binding of radiolabeled sRAGE with immobilized amyloid-beta peptide by 80%, unlabeled V-domain competed 71.4%, while C1 and C2 domains were without effect (15.2% and 21.4% competition, respectively), when all unlabeled competitors were utilized at a 100-fold molar excess (Table IV). These data indicated that only V-domain appeared to mediate the interaction with amyloid-beta peptide. These effects of unlabeled V-domain were dose-dependent; at a 100-fold molar excess, 72.5% competition was observed. At a 50-fold molar excess, 41.4% competition was observed. This was reduced to 34% at a 25-fold molar excess and to insignificant competition (3.9%) at a 10-fold molar excess of unlabeled V-domain (Table V). A series of peptides was then prepared comprising different portions of the V-domain of sRAGE. These data indicated that at an 100-fold molar excess, essentially no competition was obtained using peptides consisting of the the following amino acids of sRAGE: 1-13, 18-28, 31-60, and 46-60 (Table VI). Control peptides from C1 and C2 domains were also utilized (peptides consisting of amino acid numbers 157-169 and 270-281 of sRAGE, respectively) which had no effect (Table VI). However, peptides comprised of 1-30 of the V-domain did inhibit the binding of radiolabeled sRAGE to immobilized AGE by 29.7% (Table VI). Smaller peptides were then prepared (amino acid numbers 1-25 of sRAGE) and (amino acid numbers 10-25 of sRAGE) in an effort to further delineate the precise binding site. Even at a 100-fold molar excess, unlabeled peptide consisting of amino acid numbers 1-25 of sRAGE only inhibited the binding of radiolabeled sRAGE to immobilized amyloid-beta peptide by 5% and unlabeled 10-25 only had an 18% competitive effect (Table VI). These data suggest that a peptide consisting of amino acid numbers 1-30 of sRAGE is an effective competitor of the binding of sRAGE to immobilized amyloid-beta peptide (1-42).

DISCUSSION

The interaction of AGEs or amyloid-beta peptide with RAGE on cell surfaces likely are important contributors to the development of complications in disorders in which AGEs accumulate, such as diabetes, retinopathy, peripheral vascular neuropathy, male impotence, senile memory loss or Alzheimer's disease, respectively. Soluble or sRAGE, the extracellular two-thirds of RAGE, by blocking these effects in vitro and in in vivo models, including those of chronic diabetic complications, may have important implications as a target for drug development in these disorders.

The V-domain of sRAGE has been shown to mediate interactions of full-length sRAGE with AGEs or amyloid-beta peptide in a dose-dependent manner. Furthermore, the first 30 amino acids of the V-domain contain sequences involved in mediating these interactions. It is likely, however, that not all amino acids present within the 1-30 amino acids of sRAGE are necessary for this binding. It is also possible that a small number of amino acids beyond the first 30 amino acids of sRAGE (that is, of the V-domain) comprise an interaction site for AGE or amyloid -beta ligands. The present invention provides for compounds and compositions which would comprise polypeptides comprising such amino acids as discussed hereinabove.

A review of the sequences obtained from GenBank of the first 30 amino acids of the V-domain among human, mouse, rat and bovine species reveals remarkable homology (Table VII). For example, of the first 10 amino acids of the V-domain, complete identity among the species exists at amino acid residues 2-9 (8 of the first 10 amino acids). Of the next 10 amino acids of the V-domain (11-20), identity among the species exists at 7 of the 10 amino acids including amino acids 11, 12, 14, 16, 17, 19 and 20. Of amino acids 21-30 of the V-domain, identity among the four species exists at 8 of the 10 amino acids including amino acids 21, 22, 23, 25, 27, 28, 29 and 30.

Overall, therefore, there is 76% amino acid identity among the four species tested thus far. These data are consistent with the concept that sequences critical to the binding of AGEs or amyloid-beta peptide with sRAGE may be contained within the first 30 amino acids of the V-domain.

Taken together, these data indicate that the first 30 amino acids of the V-domain are important in mediating the interaction of sRAGE with either AGEs or amyloid-beta peptide. This suggests that the V-domain region is likely an important target for the development of drugs designed to treat disorders in which AGEs accumulate, such as in diabetic complications, aging, renal failure, amyloidoses, retinopathy, peripheral vascular neuropathy, male impotence, senile memory loss and Alzheimer's disease.

TABLE I

The V-Domain of sRAGE mediates the interaction with AGEs. Binding assays were performed as described above; radiolabeled sRAGE was bound to immobilized AGE in the presence or absence of the indicated molar excesses of unlabeled competitor. In these assays, therefore, the nearer the value is to 100%, the more effective a competitor of the binding of radiolabeled sRAGE to immobilized AGE.

| Unlabeled competitor | Fold-molar excess | % competition/$^{125}$I-sRAGE |
|---|---|---|
| full length sRAGE | 50 | 83% |
| V domain | 50 | 89 |
| C1 | 50 | 30 |
| C2 | 50 | 19 |

TABLE II

V-domain inhibits the binding of radiolabeled sRAGE to immobilized AGE in a dose-dependent manner. Binding assays were performed as described above, radiolabeled sRAGE was bound to immobilized AGE in the presence of the indicated molar excesses of unlabeled V-domain.

| Unlabeled competitor | fold-molar excess | % competition/125 I-sRAGE |
|---|---|---|
| V-domain | 100 | 80 |
| V-domain | 50 | 86 |
| V-domain | 25 | 76 |
| V-domain | 12.5 | 53 |
| V-domain | 6.25 | 28 |
| V-domain | 3.12 | 16 |
| V-domain | 1.56 | 0 |

TABLE III

The First 30 amino acids of the V-Domain of sRAGE mediate the interaction with AGEs. Binding assays were performed as described above; radiolabeled sRAGE was bound to immobilized AGE in the presence of the indicated molar excesses of unlabeled peptide.

| Peptide/V-domain [amino acid #s] | Fold-Molar Excess | % Competition/ $^{125}$I-sRAGE |
|---|---|---|
| 1–30 | 100 | 77 |
|  | 50 | 78 |
|  | 25 | 76 |
|  | 1 | 0 |
| 1–25 | 50 | 31 |
|  | 25 | 24 |
|  | 1 | 0 |

TABLE III-continued

The First 30 amino acids of the V-Domain of sRAGE mediate the interaction with AGEs. Binding assays were performed as described above; radiolabeled sRAGE was bound to immobilized AGE in the presence of the indicated molar excesses of unlabeled peptide.

| Peptide/V-domain [amino acid #s] | Fold-Molar Excess | % Competition/ $^{125}$I-sRAGE |
|---|---|---|
| 10–25 | 50 | 26 |
|  | 25 | 17 |
|  | 1 | 0 |
| 16–30 | 100 | 69 |
|  | 50 | 73 |
|  | 25 | 20 |
|  | 1 | 0 |
| 31–60 | 100 | 25 |
|  | 50 | 11 |
|  | 25 | 0 |
|  | 1 | 0 |
| 46–60 | 100 | 0 |
|  | 50 | 0 |
|  | 25 | 0 |
|  | 1 | 0 |
| 1–13 | 100 | 0 |
|  | 50 | 0 |
|  | 25 | 0 |
|  | 1 | 0 |
| 18–28 | 100 | 0 |
|  | 50 | 0 |
|  | 25 | 0 |
|  | 1 | 0 |
| 157–169 | 100 | 3 |
|  | 50 | 0 |
|  | 25 | 0 |
|  | 1 | 0 |
| 270–281 | 100 | 0 |
|  | 50 | 0 |
|  | 25 | 0 |
|  | 1 | 0 |

TABLE IV

The V-Domain of sRAGE mediates the interaction with amyloid-beta peptide. Binding assays were performed as described above; radiolabeled sRAGE was bound to immobilized amyloid-beta peptide in the presence or absence of the indicated molar excesses of unlabeled competitor. In these assays, therefore, the nearer the value is to 100%, the more effective a competitor of the binding of radiolabeled sRAGE to immobilized amyloid-beta peptide.

| Unlabeled competitor | fold-molar excess | % competition/$^{125}$I-sRAGE |
|---|---|---|
| full length sRAGE | 100 | 80% |
| V-domain | 100 | 71.5 |
| C1-domain | 100 | 15.2 |
| C2-domain | 100 | 21.4 |

TABLE V

V-domain inhibits the binding of radiolabeled sRAGE to immobilized amyloid-beta peptide in a dose-dependent manner. Binding assays were performed as described above, radiolabeled sRAGE was bound to immobilized amyloid-beta peptide in the presence of the indicated molar excesses of unlabeled V-domain.

| Unlabeled competitor | fold-molar excess | % competition/$^{125}$I-sRAGE |
|---|---|---|
| V-domain | 100 | 72.5 |
| V-domain | 50 | 41.4 |
| V-domain | 25 | 34 |
| V-domain | 10 | 3.9 |

TABLE VI

The First 30 amino acids of the V-Domain of sRAGE mediate the interaction with amyloid-beta peptide. Binding assays were performed as described above; radiolabeled sRAGE was bound to immobilized amyloid-beta peptide in the presence of the indicated molar excesses of unlabeled peptide.

| Unlabeled competitor amino acid # | fold-molar excess | % competition/$^{125}$I-sRAGE |
|---|---|---|
| 1–30 | 100 | 55 |
| 16–30 | 100 | 29.7 |
| 1–25 | 100 | 5 |
| 10–25 | 100 | 18 |
| 31–60 | 100 | 2.6 |
| 46–60 | 100 | 0 |
| 1–13 | 100 | 0 |
| 18–28 | 100 | 27 |
| 157–167 | 100 | 0 |
| 270–281 | 100 | 0 |

TABLE VII

Comparison of the First 30 Amino acids of the V-domain of sRAGE among the human, murine, rate and bovine species. Amino acid sequence of the first 30 amino acids of the V-domain are indicated for the four indicated species. Letter indicate amino acids as follows: A, ala; C, cys; D, asp; E, glu; F, phe, G, gly; H his; I, ile; K, lys; L, leu; M, met; N, asn; P, pro; Q, gln; R, arg; S, ser; T, thr; V, val; W, trp; and Y, tyr.

| | 1-10 | | | | | | | | | |
|---|---|---|---|---|---|---|---|---|---|---|
| Human | A | Q | N | I | T | A | R | I | G | B |
| Mouse | G | Q | N | I | T | A | R | I | G | E |
| Rat | G | Q | N | I | T | A | R | I | G | B |
| Bovine | D | Q | N | I | T | A | R | I | G | K |
| | 11-20 | | | | | | | | | |
| Human | P | L | V | L | K | C | K | G | A | P |
| Mouse | P | L | V | L | S | C | K | G | A | P |
| Rat | P | L | M | L | S | C | K | A | A | P |
| Bovine | P | L | V | L | N | C | K | G | A | P |
| | 21-30 | | | | | | | | | |
| Human | K | K | P | P | Q | R | L | E | W | K |
| Mouse | K | K | P | P | Q | Q | L | E | W | K |
| Rat | K | K | P | T | Q | K | L | E | W | K |
| Bovine | K | K | P | P | Q | Q | L | E | W | K |

Example 2 sRAGE Suppresses Accelerated Periodontal Disease in Diabetic Mice

A model of accelerated periodontal disease in diabetic mice and the effects of sRAGE were studied. Efficacy of sRAGE is shown in diabetic (streptozotocin C57BL6/J mice). Administration of soluble RAGE (full-length extracellular form of approximately 40 kDa) inhibits accelerated alveolar bone loss, which is the hallmark of periodontal disease.

Intraperitoneal injection of soluble RAGE suppresses bone loss in diabetic mice (db+/db+).

Administration of Soluble (s) RAGE suppresses alveolar bone loss in a murine model of accelerated periodontal disease in diabetes.

Diabetes was induced in C57BL6/J mice by administration of streptozotocin. Diabetes was defined as two serial measurements of serum glucose $\geq 300$ mg/dl. Alternatively, an equal number of mice were treated with vehicle for streptozotocin, phosphate buffered saline. One month after induction of diabetes, mice were treated every other day for four consecutive days with oral/anal administration of the human periodontal pathogen, *Porphyromonas gingivalis* (Pg) or vehicle, phosphate-buffered saline. Two months later, mice were sacrificed and decapitated. The mandibles were isolated and, under a dissecting microscope (Olympus), and using curved microdissecting forceps (2¾ inches, 0.6 mm wide) and a scalpel with a No. 15C blade, the lingual gingival tissue from the posterior area of each quadrant was dissected. Beginning with a horizontal sulcular incision at the gingival margin of the posterior teeth, the gingiva was reflected (full thickness) with the scalpel blade. Vertical release incisions were made and the tissue was removed (separating the tissue with a horizontal incision just below the mucogingival junction). Tissue was then placed in formalin (10%) for further analysis.

After the above procedures, mandibles were exposed to KOH (2%) for three days and then mechanically defleshed. The jaws (exposure of the lingual surfaces of each ½ mandible) were then embedded in lab putty. In order to remove angulation as a variable, the buccal and lingual cusps of the posterior teeth in the ½ mandible were superimposed during embedding and viewed from the lingual surface prior to photography. The defleshed jaws were photographed using the magnifying dissecting microscope and Ektachrome® 160T film (color slides).

These slides, at a magnification of 40x, were then magnified further 4x. Images were then traced onto standard tracing paper. For each mouse, a total area of the distance between the cemento-enamel junction (CEJ) and alveolar bone crest (BC) for a total of 6 posterior teeth was measured by scanning the tracing into a Macintosh® computer/scanner and the images analyzed using the program NIH Image 157® (along with Adobe Photoshop® photography program). Total area (in arbitrary pixel units) is reported for each mouse (6 teeth) as indicated in FIG. 1. Statistical analysis was performed using one way analysis of variance. At two months, a significant 1.55-fold increase in alveolar bone loss was observed in diabetic mice compared with nondiabetic controls (see specific data below). Similar results were observed in db+/db+ mice (genetically-diabetic/insulin-resistant) one month after infection with Pg compared with nondiabetic controls (m+/db+).

In order to test if administration of sRAGE would ameliorate alveolar bone loss in Pg-treated C57BL6/J mice, certain diabetic mice were treated with sRAGE (MSR; either 35 µg IP/day for two months or 3.5 µg IP/day for two months). Control diabetic mice were treated with equimolar concentrations of mouse serum albumin (70 µg IP/day for two months). All mice were treated with Pg. At the end of that time, measurements of alveolar bone loss were made. The results are as follows:

| Condition | Alveolar bone loss (CEJ to alveolar BC) |
|---|---|
| (I) Diabetic/albumin | 6,222 ± 406 pixels (SD) |
| (II) Nondiabetic/albumin | 4,018 ± 501 pixels (SD) |
| (III) Diabetic/MSR(35 µg/day) | 5,242 ± 463 pixels (SD) |
| (IV) Diabetic/MSR(3.5 µg/day) | 6,198 ± 427 pixels (SD) |

Many diabetic complications may result from the interaction of AGE's with RAGE to cause cellular perturbation. AGE acts as a ligand for the V-domain of RAGE to mediate such cellular perturbation. This invention provides a method for inhibiting cellular perturbation in a subject associated with a diabetic condition which comprises administering to the subject an amount of an inhibitor of the interation of AGE's with RAGE on the surface of a cell effective to inhibit the interaction and thereby inhibit the cellular perturbation in the subject and treat the diabetic condition.

AGE (advanced glycation endproducts) are a heterogeneous group of compounds. A single or specific pathogenic AGE compound (s) are being identified. Examples of AGEs include but are not limited to: pentosidine (alone or protein-bound modification); carboxymethyllysine (alone or protein-bound modification); carboxyethyllysine (alone or protein-bound modification); pyrallines (alone or protein-bound modification); methylglyoxal (alone or protein-bound modification) and ethylglyoxal (alone or protein-bound modification). One of these AGE's may be a pathogenic ligand for a specific cellular perturbation due to an interaction of the AGE with the V-domain of RAGE. This interaction may be a critical contributory factor in many complications associated with diabetes. This invention provides for inhibitors of such an interaction which may be administered to subjects with diabetic complications.

Cells which may be acted upon by this binding of AGE's to RAGE on the cell surface include endothelial cells, vascular smooth muscle cells, neuronal cells, macrophages, lymphocytes, retinal vascular cells, retinal neuronal cells, mesangial cells and connective tissue cells and cells associated with connective tissue such as cells associated with gingiva and skin. Cells which may be acted upon by this binding of AGE's to RAGE are not limited to this list but may include other cells present in a human body. The present invention provides compounds and compositions which may be useful in inhibiting this interaction, thereby ameliorating the cellular perturbation and ultimately the symptoms associated with diabetes.

Cellular perturbations in those cells that sRAGE, or other peptides or agents provided for by the present invention include but are not limited to: oxidant stress, hyperpermeability, enhanced expression of adhesion molecules such as Vascular Cell Adhesion Moleucle—1; enhanced expression of tissue factor; enhanced macrophage chemotaxis and activation, such as with increased production of cytokines and growth factors; enhanced migration of smooth muscle cells, activation of smooth muscle cells, neuronal oxidant stress and apoptosis. Advanced glycation endproducts (AGE) are the irreversible result of nonenxymatic glycation and oxidation. These AGE's form in the connection with a number of conditions such as: aging, diabetes, inflammation, renal failure, amyloidoses, and hyperlipidemia. AGE's also form in connection with other disease states and abnormal conditions which are not explicitly listed herein but which are encompassed by the present invention.

Example 3

Therapeutic Agents Identified Through in vitro Means, are Shown to be Effective in vivo for Inhibition of Symptoms Associated with Diabetic Complications The therapeutic agent identified may be shown to be effective in wound healing. In wound healing experiments, the secondary intention wound model in genetically diabetic mice would be used. The agent (or peptide or pharmaceutical composition) is applied topically to the wounded area, and wound closure (change in wound area), epithelialization and other histologic indices (such as collagen production, extracellular matrix production, fibrin, etc.) is measured. Each of these measurements are indices of the effectiveness of the agent on increasing wound healing.

In periodontal disease, genetically diabetic and streptozotocin-treated mice are utilized as animal model systems to examine bone loss after treatment with peptides having the sequence of SEQ ID No: 1. Bone loss is measured quantitatively via histological methods and geometrical area determinations. The peptide of SEQ ID No: 1, V-domain peptide, agent or pharmaceutical composition is administered locally (e.g. "painting on" the agent) and/or systemically. Reduced bone loss is an indication of an effective agent.

In accelerated atherosclerosis, streptozotocin-treated apoE "knock-out" mice on a normal chow diet are employed as animal models of this disease condition. The agent (or peptide or pharmaceutical composition) is administered systemically, and quantitative data is gathered by measuring lesion area in the animals after treatment. This data gives an indication of the effectiveness of each agent. The smaller the lesion area as compared to non-treated controls, the more effective the agent.

In diabetic impotence, a rat model with streptozotocin-treated animals is employed in which erections are monitored following administration of apomorphine. The number and frequency of erections is measured in the presence and in the absence of the agent and such data is compared so as to evaluate the effectiveness of the agent to inhibit symptoms of impotence.

In diabetic retinopathy, diabetic rat and mouse models are used as animal model systems to measure changes in blood flow and retinal pathology. Again, the agent (or peptide or pharmaceutical composition) is administered systemically, and quantitative data is gathered by blood flow and qualitative data is gathered by examining retinal pathology in the animals after treatment.

In diabetic nephropathy, diabetic mice and rat models are employed as animal models of diabetic nephropathy. Changes in glomerular filtration rate and renal blood flow are measured in animals given a therapeutic agent and measured in animals given a placebo. In addition, the appearance of protein in the urine and histologic changes in glomeruli are determined in each animal. The effectiveness of the agent is evaluated based upon these measurements in inhibiting diabetic nephropathy.

In diabetic neuropathy, genetically diabetic mice are utilized as an animal model for the determination of the effectiveness of the agent of the present invention. The mice are treated with the compound systemically. The mice are then observed to determine changes in nerve conduction velocity and changes in the number of myelinated peripheral nerve fibers. Such data compared with equivalent measurements determined in an untreated animal will provide an indication of the effectiveness of the agent of the present invention.

REFERENCES

Abraham, C., et al. (1988) Cell 52, 487–501;
Baron et al., Cell, 28, 395–404 (1982);
Baynes, J. Role of oxidative stress in development of complications in diabetes. Diabetes 40:405–412, 1991;
Behl, C., et al. (1994) Cell 77, 817–827;
Breslow. Mouse Models of Atherosclerosis, Science 272: 685 (1996);
Brett, J., Schmidt, A- M., Zou, Y- S, Yan, S- D, Weidman, E., Pinsky, D., Neeper, M., Przysiecki, M., Shaw, A., Migheli, A., and Stern, D., Tissue distribution of the receptor for advanced glycosylation endproducts (RAGE): expression in smooth muscle, cardiac myocytes, and neural tissue in addition to the vasculature. Am. J. Pathol. 143:1699–1712, 1993;
Brownlee, M., Cerami, A., and Vlassara, H. Advanced glycosylation end products in tissue and the biochemical basis of diabetic complication. N. Engl. J. Med. 318:1315–1320, 1988;
Calligaro, D., et al. (1993) J. Neurochem. 60:2297–2303;
Carpenter, et al. (1971) Toxicol. Appl. Pharmacol., 18:35–40;
Crall F V J and W C Roberts. The extramural and intramural coronary arteries in juvenile diabetes mellitus: analysis of nine necropsy patients aged 19 to 38 years with onset of diabetes before age 15 years. Am. J. Med. 64:221–230, 1978;
Davis, J., et al. (1992) BERC 189:1096–1100;
Dressman et al., Nature, 295, 185–160 (1982);
Fraser, P., et al. (1992) J. Neurochem. 59:1531–1540;
Fraser, P., et al. (1993) J. Neurochem. 61:298–305;
Ghiso, J., et al. (1993) Biochem. J. 293:27–30;
Gibbons and Szau. Molecular Therapies for Vascular Disease. Science 272:689–693 (1996);
Goedert, M. (1993) Trends Neurosci. 16:460–465;
Haass, C. and Selkoe, D. (1994) Cell 7:1039–1042;
Hamby R I et al. Reappraisal of the role of the diabetic state in coronary artery disease. Chest 2:251–257, 1976;
Harper's Biochemistry, R. K. Murray et al. (Editors) 21st Edition, (1988) Appelton & Lange, East Norwalk, Conn.;
Hensley, K., et al. (1994) PNAS(USA) 91:3270–3274;
Hicks, M., Delbridge, L., Yue, D. And Reeve, R. Catalysis of lipid peroxidation by glucose and glycosylated proteins. Biochem. Biophys. Res. Commun. 151:649–655, 1988;
Joslin, G., et al. (1991) J. Biol. Chem. 266:21897–21902;
Kaiser et al. Science, 223, 249–255 (1984);
Kannel W B and D L McGee. Diabetes and cardiovascular disease: the Framingham study. J. Am. Med. Assoc. 241:2035–2038, 1979;
Kimura, H., and Schubert, D. (1993) PNAS(USA) 90:7508–7512;
Kisilevsky, R., et al. (1995) Nature Med. 1:143–148;
Koh, J- Y., et al. (1990) Brain Res. 533:315–320;
Koo, E., et al. (1993) PNAS(USA) 90:4748–4752;
Kosik, K. (1994) J. Cell. Biol. 127:1501–1504;
Lander, H. L., Tauras, J. M., Ogiste, J. S., Moss, R. A., and A. M. Schmidt. Activation of the Receptor for Advanced Glycation Endproducts triggers a MAP Kinase pathway regulated by oxidant stress. J. Biol. Chem. 272:17810–17814, 1997;
Lerner et al., Cell, 23, 309–310 (1981);
Lerner, Scientific American, 248, 66–74 (1983);
Loo, D., et al. (1993) PNAS(USA) 90:7951–7955;
Manson J E et al. A prospective study of maturity-onset diabetes mellitus and risk of coronary heart disease and stroke in women. Arch. Of. Int. Med. 151:1141–1137, 1991;

Meda, L., et al. (1995) Nature 374, 647–650;

Mitsuhashi, M., et al. (1991) Mol. Brain. Rs. 11:177–180;

Miyata, T., O. Hori, J. H. Zhang, S. D. Yan, L. Ferran, Y. Iida, and A. M. Schmidt. The Receptor for Advanced Glycation Endproducts (RAGE) mediates the interaction of AGE-$\beta_2$-Microglobulin with human mononuclear phagocytes via an oxidant-sensitive pathway: implications for the pathogenesis of dialysis-related amyloidoses. J. Clin. Invest. 98: 1088–1094, 1996;

Neeper, M., Schmidt, A. M., Brett, J., Yan, S. D., Wang, F., Pan, Y. C., Elliston, K., Stern, D., and Shaw, A. Cloning and expression of RAGE: a cell surface receptor for advanced glycation end products of proteins. J. Biol. Chem. 267:14998–15004, 1992;

Park, L., Raman, K. G., Lee, K. J., Lu, Y., Ginsberg, M. D., Ferran, L., Stern, D. and Schmidt, A. M. A murine model of accelerated diabetic atherosclerosis: suppression by soluble receptor for advanced glycation endproducts. Circulation Supplement, 1997;

Pike, C., et al. (1993) Neurosci. 13:1676–1687;

Porte and Schwartz. Diabetes Complications: Why is Glucose Potentially Toxic? Science 272: 699–700 (1996);

Pyorala K M, M Laasko and M Uusitupa. Diabetes and atherosclerosis: an epidemiologic view. Diab. Metab. Rev. 3:463–524, 1987;

Robertson W B and J B Strong. Atherosclerosis in persons with hypertension and diabetes mellitus. Lab. Invest. 18: 538–551, 1968;

Ross et al., *Nature,* 294, 654–658 (1981);

Ruderman, N., Williamson, J., and Brownlee, M. Glucose and diabetic vascular disease. FASEB J. 6:2905–2914, 1992;

Schmidt, A. M., O. Hori, J. Chen, J. F. Li, J. Crandall, J. Zhang, R. Cao, S. D. Yan, J. Brett and D. Stern. Advanced glycation endproducts interacting with their endothelial receptor induce expression of vascular cell adhesion molecule-1 (VCAM-1): a potential mechanism for the accelerated vasculopathy of diabetes. J. Clin. Invest. 96:1395–1403, 1995;

Schmidt, A. M., Yan, S. D., Brett, J., Mora, R., and Stern, D. Regulation of mononuclear phagocyte migration by cell surface binding proteins for advanced glycosylation endproducts. J. Clin. Invest. 92:2155–2168, 1993;

Schmidt, A. M., Hasu, M., Popov, D., Zhang, J. H., Yan, S. D., Brett, J., Cao, R., Kuwabara, K., Costache, G., Simionescu, N., Simionescu, M., and Stern, D. The receptor for Advanced Glycation Endproducts (AGEs) has a central role in vessel wall interactions and gene activation in response to AGEs in the intravascular space. PNAS (USA) 91: 8807–8811, 1994;

Schmidt, A. M., Vianna, M., Gerlach, M., Brett, J., Ryan, J., Kao, J., Esposito, C., Hegary, H., Hurley, W., Clauss, M., Wang, F., Pan, Y. C., Tsang, T. C., and Stern, D. Isolation and characterization of binding proteins for advanced glycosylation endproducts from lung tissue which are present on the endothelial cell surface. J. Biol. Chem. 267:14987–14997, 1992;

Schwarzman, A., et al. (1994) PNAS(USA) 91, 8368–8372;

Sell, D. and Monnier, V. Structure elucidation of a senescence cross-link from human extracellular matrix: implication of pentoses in the aging process. J. Biol. Chem. 264:21597–21602, 1989;

Snow, A., et al. (1994) Neuron 12, 219–234;

Strittmatter, W. (1993a) PNAS(USA) 90, 1977–1981;

Strittmatter, W. (1993b) Exptl. Neurol. 122, 327–334;

Trojanowski, J. and Lee, V. (1994) Am. J. Pathol. 144:449–453.

Waller B F et al. Status of the coronary arteries at necropsy in diabetes mellitus with onset after age 30 yrs: analysis of 229 diabetic patients with and without clinical evidence of coronary heart disease and comparison to 183 control subjects. Am. J. Med. 69:498–506, 1980;

Walter et al., *Proc. Natl. Acad. Sci. USA,* 78, 4882–4886 (1981);

Wautier, J. L., C. Zoukourian, O. Chappey, M. P. Wautier, P. J. Guillausseau, R. Cao, O. Hori, D. Stern and A. M. Schmidt. Receptor-mediated endothelial cell dysfunction in diabetic vasculopathy: soluble receptor for advanced glycation endproducts blocks hyperpermeability. J. Clin. Invest. 97:238–243, 1996;

Wishik, C. (1989) Curr. Opin. Cell Biol. 1, 115–122;

Wong et al., Proc. Natl. Sci. USA, 79, 5322–5326 (1982);

Wu, J., Rogers, L., Stern, D., Schmidt, A. M. and Chiu, D. T. W. The soluble receptor for Advanced Glycation Endproducts (sRAGE) ameliorates impaired wound healing in diabetic mice. Abstract booklet, Plastic Surgery Research Council. Abstract #77, p. 43, 1997;

Yan, S. D., Schmidt, A. M. Anderson, G., Zhang, J., Brett, J., Zou, Y. S., Pinsky, D., and Stern, D. Enhanced cellular oxidant stress by the interaction of advanced glycation endproducts with their receptors/binding proteins. J. Biol. Chem. 269:9889–9897, 1994;

Yan, S D, X. Chen, J. Fu, M. Chen, H. Zhu, A. Roher, T. Slattery, M. Nagashima, J. Morser, A. Migheli, P. Nawroth, G. Godman, D. Stern and A. M. Schmidt. RAGE and amyloid-$\beta$ peptide neurotoxicity in Alzheimer's disease. Nature 382:685–691, 1996;

Yan, S D, Zhu, H., Fu, J., Yan, S. F., Roher, A., Tourtellotte, W., Rajavashisth, T., Chen, X., Stern, D. and Schmidt, A. M. Amyloid-beta peptide-RAGE interaction elicits nauronal expression of M-CSF: a proinflammatory pathway in Alzheimer's disease. Proc. Natl. Acad. Sci. 94:5296–5301, 1997;

Yankner, B., et al. (1990) Science 250:279–282, 1990.

---

What is claimed is:

1. A polypeptide consisting of the sequence A-Q-N-I-T-A-R-I-G-E-P-L-V-L-K-C-K-G-A-P-K-K-P-P-Q-R-L-E-W-K (Seq. I.D. No. 1), and wherein the polypeptide binds to amyloid-beta peptide.

2. A composition which comprises the polypeptide of claim 1 and a pharmaceutically acceptable carrier.

3. The pharmaceutical composition of claim 2, wherein the carrier is a diluent, an aerosol, a topical carrier, an aqueous solution, a nonaqueous solution or a solid carrier.

4. The pharmaceutical composition of claim 2, wherein the carrier is a polymer or a toothpaste.

* * * * *